United States Patent
Pang et al.

(10) Patent No.: US 9,513,226 B2
(45) Date of Patent: Dec. 6, 2016

(54) NANOCHIP BASED SURFACE PLASMON RESONANCE SENSING DEVICES AND TECHNIQUES

(71) Applicant: The Regents of the University of California, Oakland, CA (US)

(72) Inventors: Lin Pang, San Diego, CA (US); Yeshaiahu Fainman, San Diego, CA (US)

(73) Assignee: The Regents Of The University Of California, Oakland, CA (US)

( * ) Notice: Subject to any disclaimer, the term of this patent is extended or adjusted under 35 U.S.C. 154(b) by 251 days.

(21) Appl. No.: 13/967,331

(22) Filed: Aug. 14, 2013

(65) Prior Publication Data

US 2014/0204372 A1     Jul. 24, 2014

Related U.S. Application Data

(60) Provisional application No. 61/683,046, filed on Aug. 14, 2012.

(51) Int. Cl.
    *G01J 3/44*          (2006.01)
    *G01N 21/65*       (2006.01)
    *B22F 1/00*        (2006.01)

(52) U.S. Cl.
    CPC ........... *G01N 21/658* (2013.01); *B22F 1/0044* (2013.01)

(58) Field of Classification Search
    CPC ........... G01N 21/658; G01N 27/4145; G01N 21/554; G01N 15/1434; G01N 27/447; C12Q 2565/632; B22F 1/0044
    See application file for complete search history.

(56) References Cited

U.S. PATENT DOCUMENTS

| | | | |
|---|---|---|---|
| 6,297,907 B1 | 10/2001 | Wang | |
| 6,627,067 B1* | 9/2003 | Branton | B24B 37/013 204/403.06 |
| 7,421,158 B2 | 9/2008 | Fainman et al. | |
| 2005/0153464 A1* | 7/2005 | Fainman et al. | 438/9 |
| 2006/0154399 A1* | 7/2006 | Sauer | C12Q 1/6874 438/48 |
| 2007/0229817 A1* | 10/2007 | Wang | G01N 21/658 356/301 |

(Continued)

OTHER PUBLICATIONS

H. Matthew Chen, Lin Pang, Michael S. Gordon, and Yeshaiahu Fainman, "Real-Time Template-Assisted Manipulation of Nanoparticles in a Multilayer Nanofluidic Chip," published online: Aug. 15, 2011, small 2011, 7, No. 19, 2750-2757.*

(Continued)

*Primary Examiner* — Kara E Geisel
*Assistant Examiner* — Maurice Smith
(74) *Attorney, Agent, or Firm* — Perkins Coie LLP

(57) ABSTRACT

Systems, devices and techniques are disclosed for optically detecting single molecules using nanoscale chip configurations. In one aspect, a sensing device includes a composite membrane having an array of nanochannels that form openings at opposing sides of the membrane, a first and second substrate each including channels to carry a fluid containing particles, a fluidic module that is fluidically coupled to the channels to supply the fluid, a plurality of electrodes located along the channels, and an electrical module to generate an electric field via the electrodes to effectuate an electrokinetic force within the channels to steer the particles toward the openings of the nanochannels to immobilize the particles, in which the nanochannels operate as resonant structures to amplify localized fields produced in an optical interrogation of the immobilized particles.

21 Claims, 15 Drawing Sheets

(56) References Cited

U.S. PATENT DOCUMENTS

2011/0249259 A1* 10/2011 Van Dorpe ............ B82Y 15/00
356/301
2012/0105853 A1* 5/2012 Pang et al. .................... 356/445

OTHER PUBLICATIONS

H. M. H M Chen, L. Pang, M. Gordon, Y. Fainman, "In Situ Reconfigurable Nanostructure Based System in a Biocompatible Environment," no date or publisher.*

Alivisatos, P., "The use of nanocrystals in biological detection", Nature Biotechnology, vol. 22, No. 1, Jan. 2004, pp. 47-52.

Ashkin, A.et al., "Observation of a single-beam gradient force optical trap for dielectric particles", Optics Letters May 1986, vol. 11, No. 5, pp. 288-290.

Cao, Y. C. et al., "Nanoparticles with Raman Spectroscopic Fingerprints for DNA and RNA Detection", Science 297, 2002, pp. 1536-1540.

Chan, W. C. W. et al., Quantum Dot Bioconjugates for Ultrasensitive Nonisotopic Detection, Science 1998, vol. 281, 2016-2018.

Chen, Haiping Matthew et al., "Three-dimensional composite metallodielectric nanostructure for enhanced surface plasmon resonance sensing", Applied Physics Letters 94, 2009, pp. 073117-1-073117-3.

Clarke, J et al., "Continuous base identification for single-molecule nanopore DNA sequencing", Nat. Nanotech., vol. 4, 2009, pp. 265-270.

Cui, Y. et al., "Integration of Colloidal Nanocrystals into Lithographically Patterned Devices", Nano Lett. 2004, vol. 4, No. 6, pp. 1093-1098.

Davison, S. M. et al., "Boundary effects on the electrophoretic motion of cylindrical particles: Concentrically and eccentrically-positioned particles in a capillary", J. of Colloid and Interface Science 2006, 303, pp. 288-297.

Ye, C. et al., "3-D transient electrophoretic motion of a spherical particle in a T-shaped rectangular microchannel", J. of Colloid and Interface Science 2004, 272, pp. 480-488.

Fang, Y. et al., "Measurement of the Distribution of Site Enhancements in Surface-Enhanced Raman Scattering", Science, vol. 321, 2008, pp. 388-392.

Fendler, J. H., "Self-Assembled Nanostructured Materials", Chem. Mater. 1996, 8, pp. 1616-1624.

Feng, L. et al., "Nanoscale optical field localization by resonantly focused plasmons", Optics Express, vol. 17, No. 6, 2009, pp. 4824-4832.

Grier, D. G., "A Revolution in optical manipulation", Nature 2003, vol. 424, pp. 810-816.

He, H. et al., "Fabrication of Designed Architectures of Au Nanoparticles on Solid Substrate with Printed Self-Assembled Monolayers as Templates", Langmuir 2000, 16, pp. 3846-3851.

Hu, H. H., "Direct Simulation of Flows of Solid-Liquid Mixtures", Int. J. Multiphase Flow 1996, vol. 22, No. 2, pp. 335-352.

Huang, Y. et al., "Directed Assembly of One-Dimensional Nanostructures into Functional Networks", Science 2001, vol. 291, pp. 630-633.

Kalsin, A. M. et al., "Electrostatic Self-Assembly of Binary Nanoparticle Crystals with a Diamond-Like Lattice", Science 2006, vol. 312, pp. 420-424.

Keh, H. J. et al., "Boundary effects on electrophoretic motion of colloidal spheres", J. Fluid Mech. 1985, vol. 153, pp. 417-439.

Kim, S. et al., "High-harmonic generation by resonant plasmon field enhancement", Nature, vol. 453, 2008, pp. 757-760.

Kneipp, K. et. al., "Surface-enhanced Raman scattering (SERS)—a new tool for single molecule detection and identification", Bioimaging 6, 1998, pp. 104-110.

Zheng, J. et al., "Two-Dimensional Nanoparticle Arrays Show the Organizational Power of Robust DNA Motifs", Nano Lett. 2006, vol. 6, No. 7, pp. 1502-1504.

Lavan, D. A. et al., "Small-scale systems for in vivo drug delivery", Nature Biotechnology 2003, 21, 1184-1191.

Lim, D.-K. et al., "Nanogap-engineerable Raman-active nanodumbbells for single-molecule detection", Nat. Material, vol. 9, 2010, pp. 60-67.

Ma, L.-C. et al., "Electrostatic Funneling for Precise Nanoparticle Placement: A Route to Wafer-Scale Integration", Nano Lett. 2007, vol. 7, No. 2, pp. 439-445.

Medintz, I. L. et al., "Quantum dot bioconjugates for imaging, labelling and sensing", Nature Materials 2005, 4, pp. 435-446.

Nezhad, M.P. et. al., "Room-temperature subwavelength metallo-dielectric lasers", Nat. Photonics, vol. 4, 2010, pp. 395-399.

Nie, S. et al., "Probing Single Molecules and Single Nanoparticles by Surface-Enhanced Raman Scattering" Science 1997, vol. 275, 1102-1106.

Nomura, T. et al., "An arbitrary Lagrangian-Eulerian finite element method for interaction of fluid and a rigid body", Comput. Methods Appl. Mech. Eng. 1992, 95, 115-138.

Pang, L. et al., "Controlled detection in composite nanoresonant array for surface plasmon resonance sensing", Optics Express, vol. 17, No. 17, 2009, pp. 14700-14709.

Pang, L. et al., "Spectral sensitivity of two-dimensional nanohole array surface plasmon polariton resonance sensor", Appl. Phys. Lett. 91, 2007, 123112.

Pang, L. et al., "Fabrication of two-dimensional photonic crystals with controlled defects by use of multiple exposures and direct write", Applied Optics 2003, vol. 42, No. 27, pp. 5450-5456.

Sha, M. Y. et al., "Surface-Enhanced Raman Scattering Tags for Rapid and Homogeneous Detection of Circulating Tumor Cells in the Presence of Human Whole Blood", J. Am. Chem., 2008, 130, pp. 17214-17215.

Yang, A. H. J. et al., "Optical manipulation of nanoparticles and biomolecules in sub-wavelength slot waveguides", Nature 2009, vol. 457, pp. 71-75.

Sun, Y. et al., "Shape-Controlled Synthesis of Gold and Silver Nanoparticles", Science 2002, vol. 298, pp. 2176-2179.

Tao, A. et al., "Tunable plasmonic lattices of silver nanocrystals", Nature Nanotechnology 2007, vol. 2, pp. 435-440.

Uemura, S et al., Nature, vol. 464, 2010, 1012-1018.

Warner, M. G. et al., "Linear assemblies of nanoparticles electrostatically organized on DNA scaffolds", Nature Mater. 2003, vol. 2, pp. 272-277.

Xia, Y. N. et al., "Template-Assisted Self-Assembly of Spherical Colloids into Complex and Controllable Structures", J. Adv. Funct. Mater. 2003, vol. 13, No. 12, pp. 907-918.

Xuan, X.et al., Wall effects on electrophoretic motion of spherical polystyrene particles in a rectangular poly(dimethylsiloxane) microchannel, J. of Colloid and Interface Science 2006, 296, pp. 743-748.

* cited by examiner

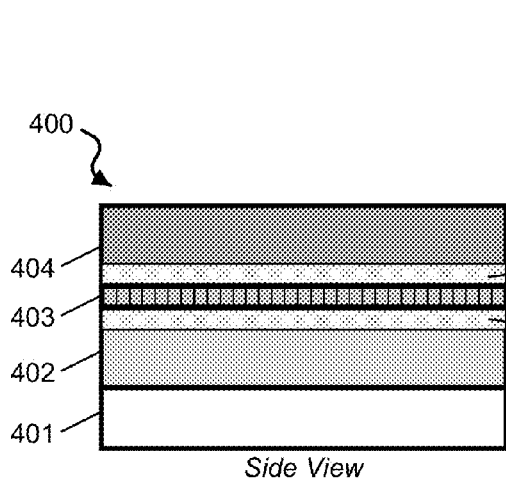
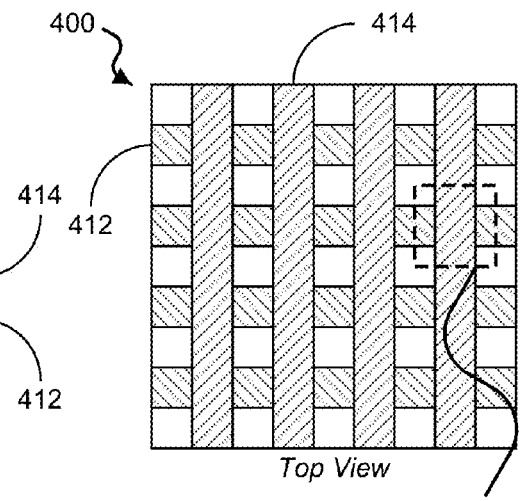
FIG. 4A  FIG. 4B
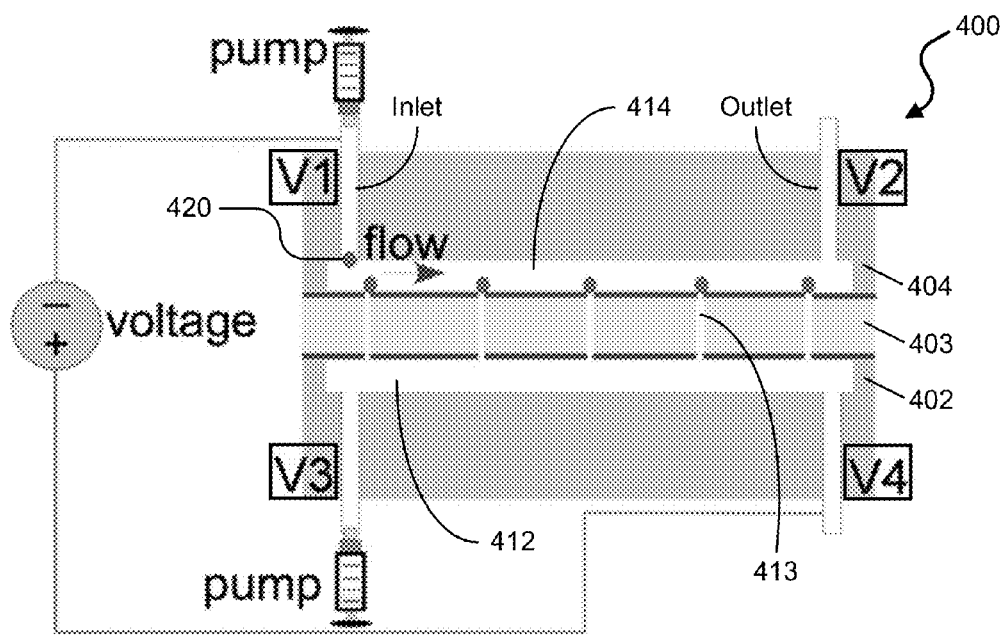
FIG. 4C

NANOCHIP BASED SURFACE PLASMON RESONANCE SENSING DEVICES AND TECHNIQUES

CROSS REFERENCE TO RELATED APPLICATIONS

This patent document claims the benefit of priority of U.S. Provisional Patent Application No. 61/683,046, entitled "NANOCHIP BASED SENSING DEVICES AND TECHNIQUES," filed on Aug. 14, 2012. The entire content of the aforementioned patent application is incorporated by reference as part of the disclosure of this application.

STATEMENT REGARDING FEDERALLY SPONSORED RESEARCH OR DEVELOPMENT

This invention was made with government support under Grant No. ECS0608863 awarded by the National Science Foundation (NSF) and Grant Nos. 67L-1083656 and HR0011-04-1-0032 awarded by the Defense Advanced Research Projects Agency (DARPA). The government has certain rights in the invention.

TECHNICAL FIELD

This patent document relates to sensing devices and sensing techniques and their applications in sensing and detecting various materials, including chemical and biological substances.

BACKGROUND

Nanotechnology provides techniques or processes for fabricating structures, devices, and systems with features at a molecular or atomic scale, e.g., structures in a range of one to hundreds of nanometers in some applications. For example, nanoscale materials can be configured to sizes similar to some large molecules, e.g., including biomolecules such as enzymes. These nanoscale materials are used to create a nanostructure, nanodevice, or a nanosystem that can exhibit various unique properties that are not present in the same materials at larger dimensions, and such unique properties of the nanoscale materials can be exploited for a wide range of applications, e.g., including the sensing of chemical or biological substances.

Chemical or biological sensors are analytical tools that can detect a chemical, substance, or organism using a sensing component coupled with a transducing element to convert a detection event into a signal for processing and/or display. For example, molecular sensors can be configured to use specific chemical properties or molecular recognition mechanisms to identify target molecular agents. The sensor can use the transducer element to transform a signal resulting from the detection of the molecular analyte by the sensing component into a different signal that can be addressed by a suitable transduction mechanism, for example, electrical, magnetic, mechanical, physicochemical, electrochemical, optical, piezoelectric, or others.

Raman spectroscopy is a quantitative and nondestructive optical technique based on inelastic scattering of photons by molecular vibrations of materials (e.g., such as biopolymers) that is capable of detecting information on the biochemical composition of cells (e.g., amino acids and proteins, lipids, and nucleic acids, among others). For example, Raman spectroscopy can be used as a bio-characterization and analysis tool to study cellular events, e.g., such as chemical changes and cell death induced by drugs or toxins, as well as cellular changes at different time points in the cell cycle. Raman spectroscopy can provide data related to physiological processes occurring within a cell without the use of chemical tags, leaving cellular functions unaltered during observations and available for repeated monitoring of time-dependent events of the same cell.

SUMMARY

Systems, devices and techniques are disclosed for detecting chemical and biological substances including single molecules based on various nanoscale chip (nanochip) design configurations.

In one aspect, a sensing device includes a nanochip component structured to include a metal layer having an array of metal nanoholes that are separated from one another, and a non-metal material layer formed on the metal layer and having an array of non-metal nanoholes that respectively align with the metal nanoholes to form an array of nanochannels that pass through the non-metal material layer and the metal layer to form openings at two sides of the nanochip component; a first substrate formed of an electrically insulative material on one side of the nanochip component and structured to include a first channel to carry a fluid containing particles; a second substrate formed of an electrically insulative material on the opposite side of the nanochip component to the first substrate and structured to include a second channel to carry the fluid; a plurality of electrodes configured in the first substrate and the second substrate, in which at least some of the electrodes are located proximate to the ends of the first and second channels; and an electrical module that is electrically coupled to the electrodes and configured to apply an electric signal to at least one electrode in the first substrate and to at least one electrode in the second substrate to generate an electric field to effectuate an electrokinetic force within the channels to steer the particles toward the openings of the nanochannels to trap the particles; in which the sensing device is operable to immobilize the particles at the openings of the nanochannels, and the nanochannels operate as resonant structures to amplify localized fields produced in an optical interrogation of the immobilized particles.

Implementations of the sensing device can optionally include one or more of the following features. For example, the particles can include a nanoparticle, a microparticle, a molecule, a virus, or a cell, among others. In some implementations, for example, the sensing device is operable to immobilize a single particle at the nanochannel. For example, the single immobilized particle or multiple immobilized particles can be assembled at a respective nanochannel based on the effective index of refraction of the nanochannel, the effective index of refraction of the particle or particles, and depth within the respective nanochannel to which the single immobilized particle or multiple immobilized particles are trapped. In some implementations, for example, the metal nanoholes in the metal layer can be structured to permit a single molecule of a size smaller than that of the opening to pass through the respective nanochannel. In some implementations, for example, the array of nanochannels can be configured as a periodic array such that the nanochip component is structured to support both propagating surface plasmon polariton (SPP) waves and localized surface plasmon resonant (LSPR) modes. In other implementations, for example, the array of nanochannels can be configured as an aperiodic or quasi-periodic array such that the nanochip component is structured to support LSPR modes. In some implementations, for example, the sensing device can further include a fluidic module that is fluidically coupled to the first and second channels to supply the fluid to the channels. For example, the fluidic module can be configured to control the fluid to flow between the first and second substrates via the nanochannels of the nanochip component. For example, the fluidic flow can be controlled by the fluidic module to provide a neutral fluidic pressure between the first and second channels. In some examples of the sensing device, the metal layer includes gold, the non-metal material includes a polymer material, and the first and second substrates include polydimethylsiloxane (PDMS). In some examples of the sensing device, the non-metal material includes a dielectric material. In some implementations, for example, the sensing device can further include an optical module that is coupled to supply light to the nanochip component to effectuate an optical trapping force to trap a molecule or particle at one end of a nanochannel. In some implementations, for example, the sensing device can further include an optical interrogation module that directs a coherent light beam on the nanochip component and detects inelastic scattering of the light beam by at least some of the trapped particles at the openings of the nanochannels to determine their Raman spectra, in which the resonant structures amplify detected signals corresponding to the inelastic scattering. In some implementations, for example, the sensing device can be used to detect a single molecule by a method including directing laser excitation light to the nanochip component to induce a localized surface plasmon resonance; and detecting an optical response signal caused by the localized surface plasmon resonance to extract information on the particles in the fluid in contact with the nanochannels.

In another aspect, a method to capture and characterize particles in a fluid includes transferring a fluid containing particles in a first channel of a nonconductive material formed over a composite membrane including an array of nanochannels that pass through two opposing sides of the composite membrane to a second channel of a nonconductive material formed on the opposing side of the composite membrane, in which the first and second channels include a plurality of electrodes positioned proximate to the ends of the first and second channels; selecting a frequency and magnitude of an electrical signal to be applied at the electrodes; applying the electrical signal to generate an electric field to effectuate an electrokinetic force within the first and second channels to steer the particles toward the nanochannels to capture one or more particles at an opening or within a respective nanochannel; directing a coherent light beam on the nanochannels of the composite membrane; detecting, using an optical device, inelastic scattering of the light beam by at least some of the particles captured at the nanochannels, in which the nanochannels operate as resonant structures to amplify localized fields produced by the inelastic scattering of the light beam of the captured particles; and determining a Raman spectra from the detected light.

Implementations of the method can optionally include one or more of the following features. For example, the composite membrane can be structured to include a metal layer having an array of metal nanoholes and a non-metal material layer attached to the metal layer and having an array of non-metal nanoholes that respectively align with the metal nanoholes to form the array of nanochannels. In some implementations, for example, the method further includes, prior to the directing the coherent light beam, supplying light to the composite membrane to effectuate an optical trapping force to supplement or replace the electrokinetic force to trap one or more particles at an opening or within a respective nanochannel. In some implementations, for example, the method further includes, prior to the applying the electric signal and using a fluidic module that is fluidically coupled to the first and second channels, controlling the fluid to flow through the nanochannels of the nanocomposite membrane to produce a neutral fluidic pressure between the first and second channels. For example, in some implementations, the array of nanochannels can be configured as a periodic array such that the composite membrane is structured to support both propagating surface plasmon polariton (SPP) waves and localized surface plasmon resonant (LSPR) modes, whereas, in other implementations, for example, the array of nanochannels is an aperiodic or quasi-periodic array such that the composite membrane is structured to support LSPR modes.

In another aspect, a nanophotonic sensor device includes a substrate of an electrically nonconductive material; and an array of three dimensional metallic nanostructures structured to include a nanoparticle mounted on a nanopillar structure coupled to the substrate, the nanoparticle including an opening having an orientation and diameter on the nanoparticle leading to an at least partially hollowed interior of the nanoparticle, in which each of the three dimensional metallic nanostructures of the array are operable to individually amplify localized fields produced in an optical interrogation of particles in contact with the respective nanoparticles of the metallic nanostructures.

Implementations of the nanophotonic sensor device can optionally include one or more of the following features. For example, the nanopillar structure can include a latitudinal dimension smaller than a corresponding latitudinal dimension of the nanoparticle. For example, the diameter of the opening can be configured to be twice the radius of the nanoparticle times the sine of an angle of the orientation. For example, the orientation of the opening can be configured to be substantially parallel to a direction of the substrate, and the diameter of the opening can be configured to be 140 nm or smaller. In some implementations, for example, the nanophotonic sensor device can be implemented as a surface enhancing Raman scattering substrate to detect uniform Raman scattering signals based on a supplied light from the optical interrogation of the particles.

The subject matter described in this patent document can be implemented in specific ways that provide one or more of the following features. For example, the disclosed nanochip sensor devices can be integrated with a fluidic delivery system to localize molecules or particles on nanoscale resonator structures for optical interrogation within a large optical field of the nanoresonator structure's cavity to reveal spectroscopic signature of the screened molecules. The disclosed nanochip devices are capable of manipulating and placing these molecules onto an area generating the maximum field intensity such that the localized fields are enhanced (e.g., $|E|^4$ enhancement) over the entire sensor area, thereby providing highly-sensitive detection regions for molecule identification down to single molecule level. The nanoscale resonator structures can be configured in a periodic, quasi-periodic, or non-periodic array on the nanochip sensor that can create spatial distribution of the enhanced Raman scattering signal by the trapped molecules at each nanoresonator structure. The disclosed nanochip sensor devices can be implemented in a variety of applications including biosensing of biochemicals and biological organisms, and molecular sensing of chemical structures and bonds, including detection of weapons of mass destruction (WMD). In some implementations, for example, the enhanced interaction field can be generated over such a small volume on the nanochip sensor that enable the ability to detect additional information at a sub-molecular level, e.g., such as the relationship of chemical bonds of the detected molecule.

These and other aspects are described in greater detail in this patent document.

BRIEF DESCRIPTION OF THE DRAWINGS

FIGS. 4A and 4B show schematic diagrams of an exemplary multilayer fluidic nanophotonic and nanoplasmonic characterization nanochip device.

FIG. 4C shows schematic diagram of the exemplary nanochip device integrated with a system to trap exemplary nanoparticles to the exemplary nanochip device.

DETAILED DESCRIPTION

Figure 1A:
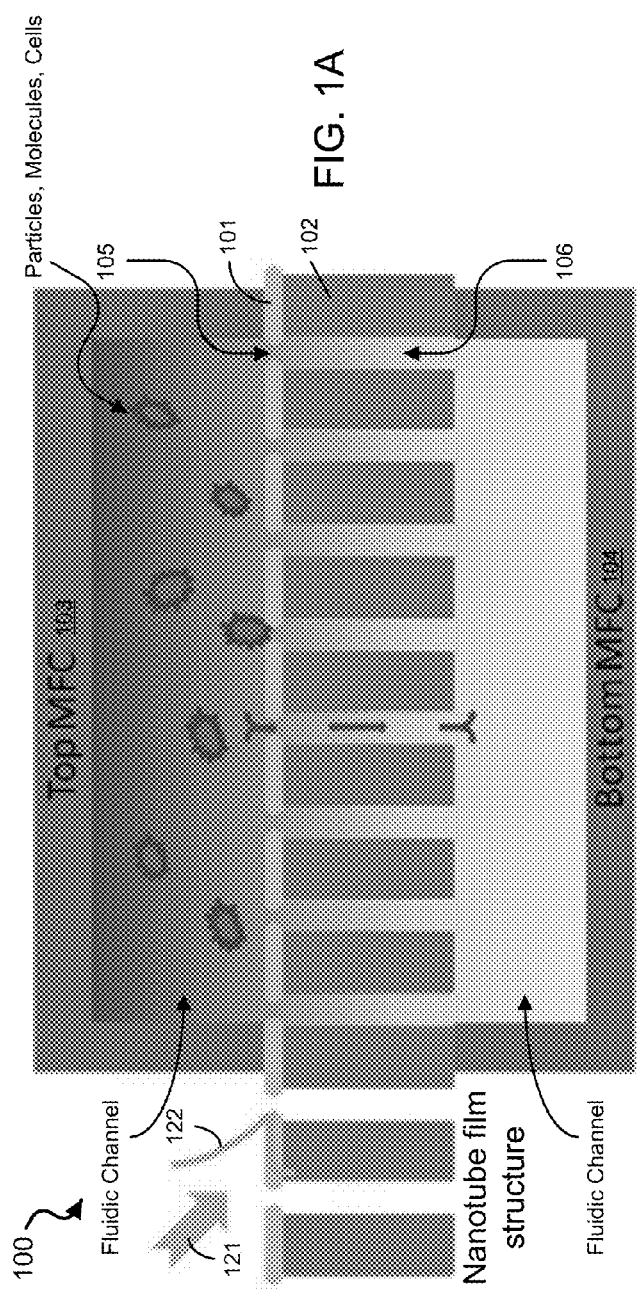
FIGS. 1A-1C show diagrams of an exemplary nanochip-based sensor device of the disclosed technology.

Various nanostructures can be constructed to exhibit certain electromagnetic properties and optical responses that can detect chemical and biological substances at or near the nanostructures, e.g., including single molecule detection. For example, plasmons are eigenmodes of collective density oscillations of quasi-free electrons or an electronic gas in metals and other materials under optical excitation. Surface plasmons are those plasmons that are confined to surfaces and that interact strongly with light, e.g., resulting in a polariton, a quasiparticle formed by plasmons coupled with a photon. For example, surface plasmons can be generated by coupling photons and electrons at or near a surface of an electrically conductive material interfacing with a dielectric material as surface plasmon polaritons (SPP).

The resonance condition for the surface plasmon resonance (SPR) is established when the frequency of light photons matches the natural frequency of surface electrons oscillating against the restoring force of positive nuclei. Surface plasmons can be excited or generated as localized surface plasmon resonance (LSPR) for nanometer-sized structures. Characterization of SPR can be used in materials sensing application, e.g., such as measuring adsorption of a material onto planar metal surfaces or the surface of metallic nanoparticles.

Some SPR sensors use SPP for sensing a change in the refractive index surrounding the metallic surface or nanostructure. In other designs, SPR sensors can be configured to use LSPR in sensing the change in the refractive index surrounding the metallic surface or nanostructure. For example, one such LSPR sensor includes nanoparticle scattering and random nanohole transmission configurations, which utilize the nanoresonant excitations induced by the particle's size and shape to sense the refractive index change around the nanostructures. In another example, surface enhanced Raman spectroscopy (SERS) can be performed in a nanostructure to identify a molecule by detecting the vibrational resonance or its fingerprint. Some examples for achieving SERS can use metallic nanoparticles, assembled nanoparticle arrays or microfabricated periodic structures (e.g., including cylindrical, pyramidal arrays) in their LSPR or propagating SPP excitation.

Systems, devices and techniques are disclosed for detecting chemical and biological substances including single molecules based on various nanoscale chip (nanochip) design configurations.

In one aspect, a sensing device includes a nanochip component structured to include a metal layer having an array of metal nanoscale holes (nanoholes) separated from one another, a non-metal material layer (e.g., dielectric material) formed on the metal layer and having an array of non-metal nanoholes that respectively align with the metal nanoholes in the metal layer to form an array of nanochannels, e.g., in which the nanochannels are formed through the aligned nanoholes in the non-metal material layer and the metal layer to connect two sides of the nanochip component. The sensing device includes a first substrate formed of an electrically insulative material on one side of the nanochip component and structured to include a first channel to carry a fluid containing particles. The sensing device includes a second substrate formed of an electrically insulative material on the opposite side of the nanochip component to the first substrate and structured to include a second channel to carry the fluid. The sensing device includes a fluidic module coupled to the first and second channels to supply the fluid to the channels, and in some implementations, control fluid flow. The sensing device is operable to immobilize the particles at the openings of the nanochannels for optical interrogation to determine the spectroscopic signature of the particles, in which the resonant structures amplify localized fields produced by Raman scattering.

In some implementations, for example, the sensing device can include a plurality of electrodes configured in the first substrate and the second substrate and located proximate to the ends of the first and second channels. For example, the sensing device can include an electronic circuit electrically coupled to the first and second electrodes to apply an electric field across at least one electrode in the first substrate and at least one electrode in the second substrate, in which the applied electric field causes an electrophoretic force to steer the particles toward the opening of the nanochannels forming a trapping region to trap the particles. In some implementations, for example, the sensing device is integrated with an optical device that directs a coherent light beam on the nanochip component and detects inelastic scattering of the light beam by at least some of the particles in the trapping region to determine their Raman spectra, in which the resonant structures amplify the detected signal of the Raman spectra.

In some implementations, the nanochip component can include a composite metallic-dielectric film including an array of nanotube structures with channels having a diameter in the nanoscale range that pass through the film between the nanotubes, in which the nanochannels function as resonant structures. The exemplary composite metallic-dielectric film is coupled to microfluidic channels, in which the resonant structures can provide the trapping of single molecules, particles, and/or cells, in which the trapped single molecule can be detected, e.g., using surface enhanced Raman spectroscopy (SERS) characterization techniques. The disclosed nanochip-based sensing devices can be used to achieve localized surface plasmon resonances (LSPR) with a maximal electric field generated from the resonant nanostructures. In operation, the integration of the nanochip and micro- and nano-fluidics can be used to effectively trap a single molecule with physical trapping forces and hold the trapped molecule with an optical force at the nanoresonance with the maximal electric field of LSPR for highly-sensitive SERS detection. In some implementations, the disclosed nanochip-based sensing devices can be used for combining and integrating single molecular sorting, detection, collection though stacking nanochip with different nanotube sizes and microfluidic control and delivery network.

In some implementations, the nanoscale resonator structures can be configured in a periodic, quasi-periodic, or non-periodic array that can create spatial distribution of the enhanced Raman scattering signal by the trapped molecules at each nanoresonator structure. For example, each element in the array can act as a point-like source that radiates the Raman signal with a broad angular distribution. The resulting wave that can be observed from the resonator elements is therefore the constructive interference of each individual wave emitted from each nanoresonator. In one implementation of a periodic array of nanoresonator structures, for example, a high coherence in both spatial and temporal domain is maintained to provide a narrow interference signature, thus leading to high sensitivity in detection.

In an exemplary embodiment, the nanochip component can be structured as a metal layer (e.g., a gold film) configured on top of a perforated non-metal membrane, in which the exemplary gold film protrudes out over the perforated membrane forming nanochannels or nanoscale voids. In one example for nanoplasmonic characterizations, localized SPR can be implemented, e.g., excited by propagating SPR through a periodic array of the nanochannels from direct illumination on the nanochip component of the sensing device. It is noted, for example, the periodicity of the nanohole array is not necessary in the disclosed designs. The periodicity can be used to generate the propagating SPR. The excited LSPR is located at the edges of the nanochannels or nanovoids.

FIG. 1A shows a schematic illustration of an exemplary nanochip device 100 of the disclosed technology. The nanochip device 100 includes a nanotube film structure having a composite metallic-dielectric film. The composite metallic-dielectric film is structured to include specially-designed resonant nanostructures on at least one side of nanotube structures of the nanotube film structure that are operable for particle, molecule, and/or cell trapping and SERS detection of the single molecule. Specifically, the nanotube film structure includes a metal layer 101 patterned to have an array of metal nanoholes 105 separated from one another and a non-metal material 102 (e.g., dielectric material) formed on the metal layer 101 and patterned to have an array of non-metal nanoholes 106 in the non-metal material 102 to align with the metal nanoholes 105. The aligned metal nanoholes 105 and the corresponding non-metal nanoholes 106 form an array of nanochannels through the nanotube film structure. The nanochip device 100 includes a first substrate 103 and a second substrate 104 formed of an electrically insulative material built on the top and bottom sides, respectively, of the nanotube film structure. The first substrate 103 can be configured as a microfluidic chamber on top of the nanotube film structure, and the second substrate 104 can be configured as the bottom microfluidic chamber, in which the first and second substrates 103 and 104 each include one or more microfluidic channels in the respective chambers for delivering a fluid containing the particles, molecules, and/or cells in a fluidic flow over the resonant nanostructures. In some implementations, the nanotube channels can be configured as intersecting holes formed of circular shapes. In other implementations, the nanotube channels can be configured in other configurations, for example, as intersecting holes formed of other shapes, including but not limited to square, rectangular, triangular, or nonuniform shapes.

In some implementations, the nanochip device 100 is operable to control the gradient of the fluid based on the pressure difference between the two exemplary chambers to trap the particles, molecules, and/or cells onto the resonant nanostructures. In other implementations, the nanochip device 100 is operable to control other forces to trap the particles at the resonant nanostructures using electrical potentials, material concentrations, and/or levels of pH values between the two microfluidic channels on the two sides of the nanotube film structure.

For example, the nanochip device 100 can be configured to induced locally concentrated electrical fields to assist capturing of single molecules, particles, or biological substances by the optical trapping force generated by the produced electric field gradient. For example, the nanotube film structure can include the nanochannels spatially separated and individual electrodes patterned along one or more sides of the nanotube film structure and/or attached microfluidic chambers to provide additional electrophoresis force to guide the substances to the trapping region. In some examples, the substances can include biomolecules including DNA strings that can be trapped within the individual nanochannels.

Figure 1C:
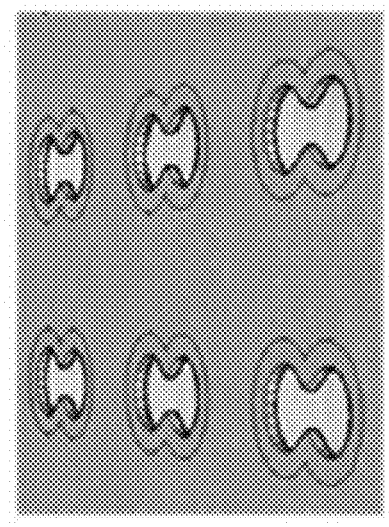
Figure 1B:
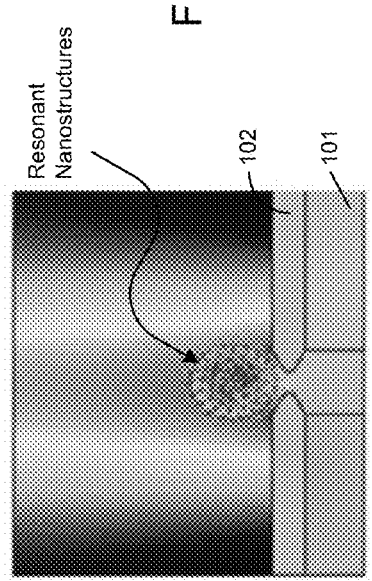

The exemplary geometry of the nanochip device 100 can induce a strong local field concentration when surface plasmonic polaritons are propagating across the exemplary metallic film and thus excite strong LSPR at the resonant nanostructures. As shown in schematic of FIG. 1A, the exemplary green arrows 121 and field distribution 122 represent an illuminating wave and corresponding SPR fields. FIG. 1B shows a diagram showing the exemplary 3D shape of deposited metal surface holes for local field enhancement. FIG. 1C shows a diagram of an exemplary resonant nanostructures. In the exemplary embodiment of the nanochip device shown in FIG. 1C, the entrance shape of the nanotube channels is configured as two intersecting circular holes. For example, the nanochip device 100 can also be used to enable SERS measurements of the trapped single substance (e.g., particle, molecule, virus, bacteria or cell) via excitation of strong localized surface plasmon resonance overlapping the trapped particle.

For example, once a molecule is trapped on a resonant nanostructure above a respective nanotube film structure, as shown in FIG. 1B, an optical interrogation technique can be performed using the nanochip device 100. For example, an optical interrogation technique can include an enhanced LSPR excitation and SERS detection. An enhanced LSPR excitation can be achieved by resonant coupling of free space waves into surface plasmonic polaritons (SPP) so that the excited SPP propagates across the exemplary metallic nanostructure and is coupled to the LSPR to create local field concentration around the trapped molecule that triggers the surface enhanced Raman scattering. For example, to produce high excitation efficiency, the SPP wave can be excited from a periodic perforation under the phase matching condition. SERS detection can be based on the Raman spectroscopy measurement in which information of the molecular vibration state signature is recorded and analyzed. Such information can be considered as the substance's molecular fingerprints that identify the chemical composition of the molecule. Since the locations of the trapping spots are well defined, the optical interrogation technique can be implemented at each individual spot to measure the property of the trapped substance and/or identify individual SERS fingerprint of each trapped substance on the nanochip device 100 with controllability and selectability. For example, by using the SPP excitation for the SERS measurement, additional advantages are provided including reduction in the noise signal that may result from the direct reflection from the sample surface, thereby improving the signal to noise ratio (SNR) of the detection.

For example, after the SERS identification, the trapped substances (e.g., single or multiple particles, molecules, viruses, bacteria, and/or cells) can then be released via controlling physical forces between the micro-fluid chambers 103 and 104 of the nanochip device 100. For example, the released molecules can be collected into a dedicated reservoir. The collection of the molecule can be achieved in various ways. For example, the nanofluidic flow through the nanotube can be turned off and the illumination light source that generates the optical trapping force can be turned off so that the molecule can be released from the trapped hole and redirected to the designated reservoir for collection. In another example, an electric voltage can be applied between the nanochip device 100 to tunnel or squeeze the substance through the nanochannel such that the particles, molecules, and/or cells can be directed and collected through microfluidic manipulation from the opposite side of the nanochip.

Figure 2:
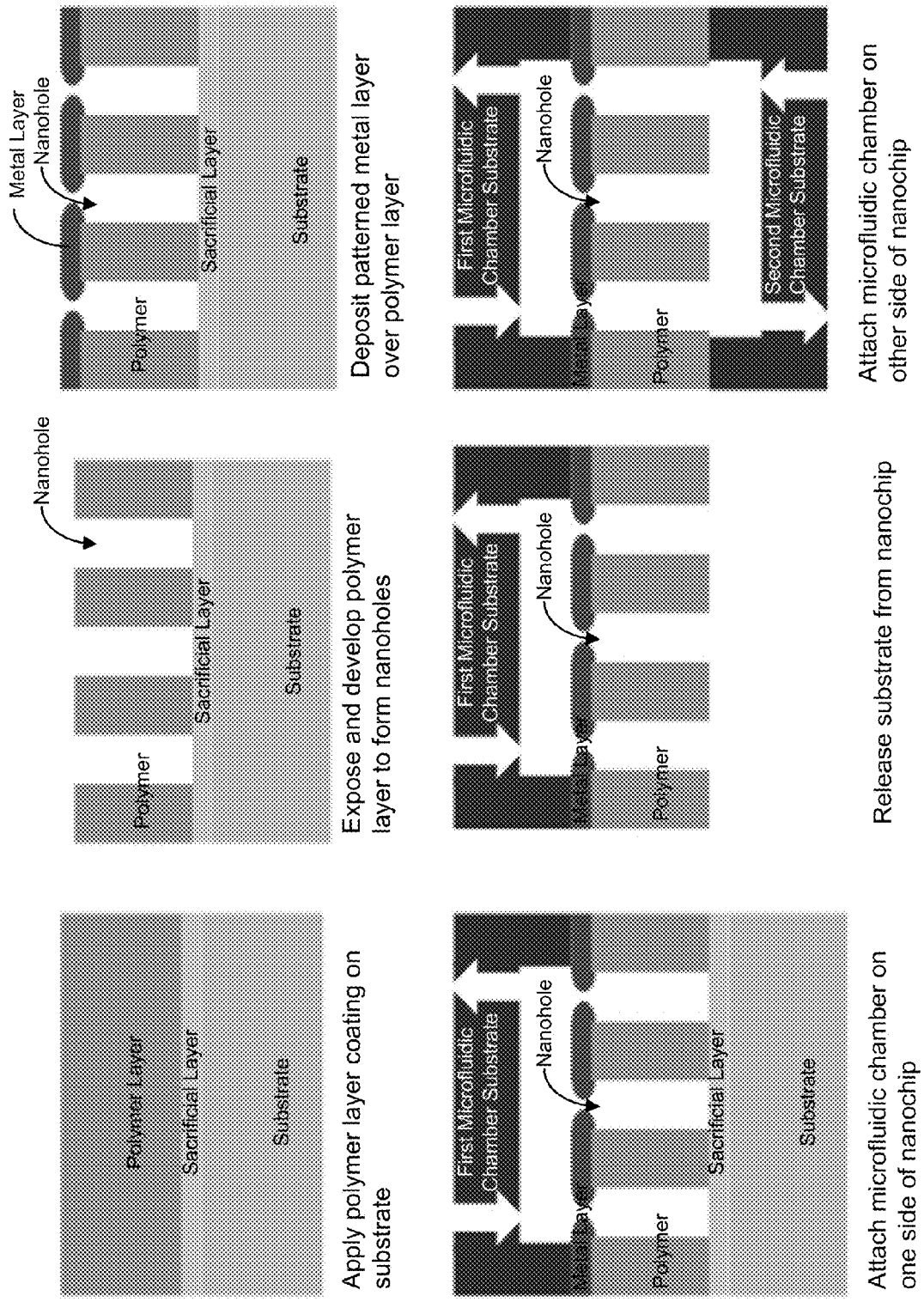
FIG. 2 shows a diagram of an exemplary fabrication process of the exemplary composite metallic-dielectric resonant nanotube film and its integration with microfluidics.

FIG. 2 shows an illustrative process diagram of an exemplary fabrication method to produce the nanochip device 100 with the microfluidic channels. The fabrication method shown in FIG. 2 includes a process to apply a polymer layer on a substrate coated by a sacrificial layer. The fabrication method includes a process to expose and develop the polymer layer to form an array of nanoscale holes, e.g., which can be implemented using holographic lithography techniques. In some examples, the nanoholes can be configured in a periodic pattern array (e.g., periodical perforations), while in other examples, the nanoholes can be configured in non-periodic patterns. The fabrication method can include a process to deposit a metal layer over the polymer layer, e.g., such that the deposited metal layer produces a metal surface shape that preserves at least some area of the openings of the nanoholes. The fabrication method includes a process to attach a first microfluidic chamber (e.g., microscale channels) including channels that align over at least some of the nanoholes. The fabrication method includes a process to remove the initial substrate from the device, e.g., via the sacrificial layer. The fabrication method includes a process to attach a second microfluidic chamber including channels that align over at least some of the nanoholes. In some examples, the first and second microfluidic chambers include inlet and outlet channels that lead to corresponding microchannels.

In some implementations of the fabrication method, for example, the process to produce the exemplary periodical perforations can be implemented using exemplary holographic lithography processes described in U.S. Pat. No. 7,421,158, which is incorporated in its entirety by reference as part of the disclosure of this patent application. Also, for example, in some implementations, the process to deposit the metal layer to produce the metal surface shapes can be implemented using exemplary techniques described in U.S. Patent Publication US2012/0105853A1, which is incorporated in its entirety by reference as part of the disclosure of this patent application.

Figures 3A, 3B:
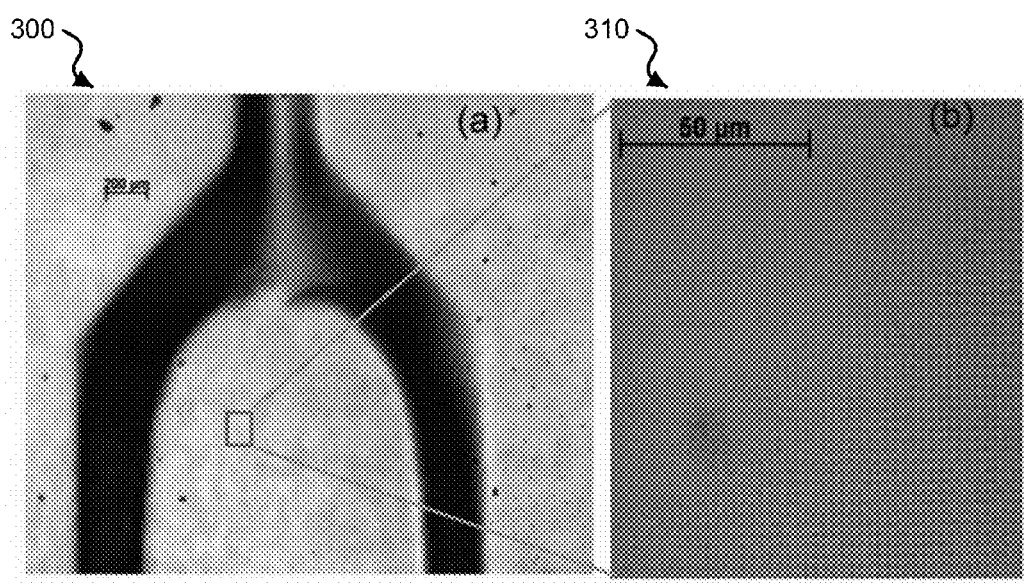
FIGS. 3A and 3B show images of an exemplary fabricated nanochip bonded on microfluidic chamber.

FIGS. 3A and 3B show microscopic images of an exemplary fabricated nanochip bonded on microfluidic chamber, e.g., in which the second microfluidic chamber was removed in order to acquire the images. The image in FIG. 3A shows the exemplary nanochip bonded on the first microfluidic channel, e.g., formed of polydimethylsiloxane (PDMS), where the bright area of the image corresponds to the nanochip due to the reflection from a metal film (e.g., Au film). The dark area of the image corresponds to the microfluidic wall due to less reflection from the deformed Au film. The area surrounded by the dark area represents the microfluidic channel sealed by the exemplary nanofilm and the PDMS. The rest area of the exemplary nanochip is bonds to the PDMS surface to support the nanochip device. The image in FIG. 3B shows a zoom-in image of the exemplary nanochip of the microfluidic channel, showing the exemplary nanochannels.

In another aspect, the disclosed technology includes real-time nanophotonic systems, devices, and processes to detect and/or characterize single particles, molecules and/or biological substances, e.g., including viruses or cells, in an aqueous, biocompatible environment employing colloidal nanostructures with lithographic patterning, applied electrical fields, and micro- and nano-fluidics to control nanoparticles into a predefined pattern based on electrokinetic forces to produce nanophotonic structure chip devices. The disclosed process can be extended to biomolecules and quantum dots in a solution based platform where various nanostructure pattern can be realized by designing the corresponding nanochannel pattern.

In some implementations, for example, chemically-synthesized nanocrystals and quantum dots can be used in an aqueous environment as essential nanomaterials for biolabeling and biosensing for single molecule detection. The quality, size and shape distribution of the nanocrystals and nanoparticles required for such applications can depend on the synthesis techniques employed to fabricate such nanostructures. For example, because of the colloidal nature of nanostructures, it can be difficult to control their position to form highly symmetric nanostructures for nanophotonic or nanoplasmonic applications. Thus, for making nanoparticle-based photonic materials and devices, fabrication processes that can produce nanomaterials with ultra-small scale and spherical, three-dimensional geometry are required.

Conventional techniques fail to produce nanostructures that are useful for nanophotonic or nanoplasmonic applications. For example, traditional lithographic methods including electron beam lithography techniques are not capable of fabricating ultra-small scale, three dimensional structures with consistent geometries. Although self-assembly techniques have made great strides by using biomimetic antibody-antigen recognition, biopolymeric scaffolding and DNA motif, and Langmuir-Blodgett technique to form highly packed structures, the real-time manipulation of nanoparticles into a regular pattern has not been demonstrated in an aqueous, biocompatible environment. In some examples, the sensitivity of a coherently-spaced, periodic nanoparticle array can be nine times higher than that of a single nanoparticle in an aqueous environment. Furthermore, precise nanoparticle manipulation is highly desired when using nanoparticles as carriers to deliver drug into specific position within an organism or in single molecule detection scheme. Although the optical tweezers can manipulate particles at the micrometer scale, it is presently not practical to use optical field for manipulation at the nanoscale due to the force decay dependence on the particle's size and the diffraction limit of focusing light down to the nanometer scale. Instead, several methods have been demonstrated for placement of nanostructures by exploiting the electrostatic potential gradient between patterned strips of chemically modified surfaces with positively and negatively charged characteristics, by combining microfluidic with surface patterning technique to align nanowires, and by using capillary forces to trap nanoparticles into lithographically predefined trenches after the drying process. However, all these techniques are static and cannot be monitored in real-time nor in vivo, where the ability to reconfigure nanophotonic structure with freshly functionalized nanoparticles would greatly benefit in vivo sensing.

FIGS. 4A and 4B show schematic diagrams of an exemplary multilayer fluidic nanophotonic and nanoplasmonic characterization nanochip device 400. The nanochip device 400 includes a substrate 401 upon which multiple layers are formed to include microfluidic and nanofluidic channels. In one exemplary embodiment, the nanochip device 400 includes a top layer 404 configured over an intermediate layer 403 configured over a bottom layer 402 configured on the substrate 401. In some embodiments, for example, the bottom layer 402 can serve as the substrate of the device 400. The top and bottom layers 404 and 402 can be formed of an electrically insulative material and are structured to include microchannels 414 and 412, respectively. In some embodiments, for example, the top and bottom layers 404 and 402 can be formed of polydimethylsiloxane (PDMS). In some embodiments, for example, the top layer 404 can be structured to include inlets on at least one side of each microchannel 414 in the layer. The intermediate layer 403 is structured to include nanochannels 413 formed from nanoscale holes (nanoholes) through the intermediate layer 403 and between the microchannels 414 and 412 in the top and bottom layers 404 and 402, respectively. For example, the size of the nanochannel can range from a few nanometers to hundreds of nanometers, depending on the application requirements.

FIG. 4C shows schematic diagram of the exemplary nanochip device 400 integrated with a system to provide fluidic flow of nanoparticles 420 in a fluid and an applied electric field to trap the nanoparticles 420 on the nanochannels 413 of the device 400. The integrated system can include a pump system to provide the fluidic flow of the fluid. This integrated system can also include a plurality of electrodes electrically coupled to an electric signal source (e.g., voltage source), in which the electrodes are configured to interface with the top layer 404 and the bottom layer 402 at various regions of the nanochip device 400. The electrode configuration can be used to produce electrokinetic forces to control the flow of the nanoparticles 420 onto the nanochannels 413. As shown in FIG. 4C, electrodes V1 and V2 are configured to the top layer 404 and are used for lateral control of the nanoparticles 420, and electrodes V3 and V4 are configured to the bottom layer 402 and are used for transverse control of the nanoparticles 420. In the example shown in FIG. 4C, either V1 and V4 or V2 and V3 are used to produce electrokinetic forces to control the flow of the nanoparticles 420 onto the nanochannels 413.

Figure 4D:
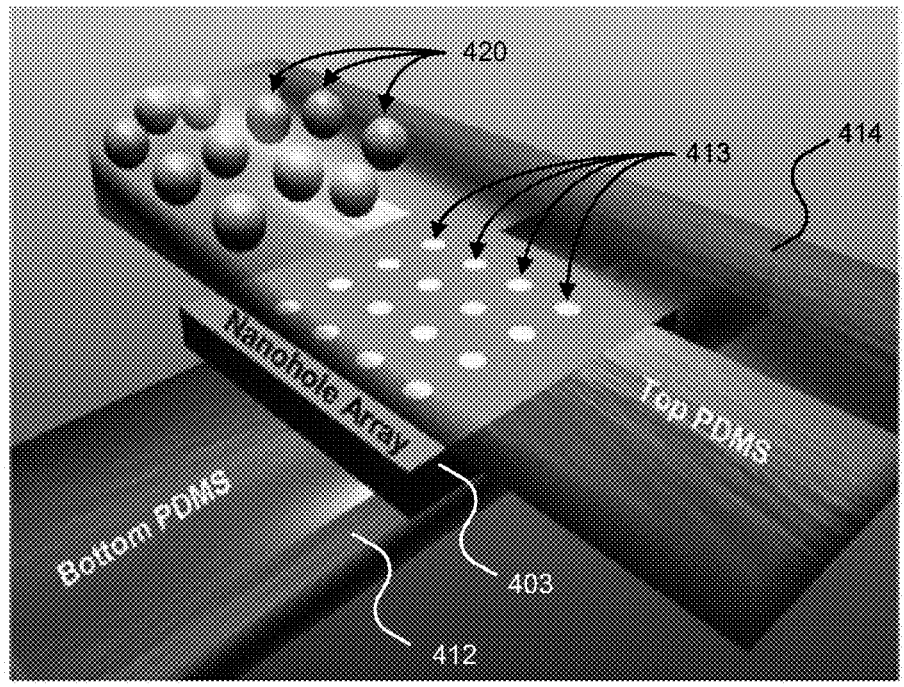
FIGS. 4D and 4E show schematic illustrations of exemplary nanoparticles trapped on nanochannels of the exemplary nanochip device.
Figure 4E:
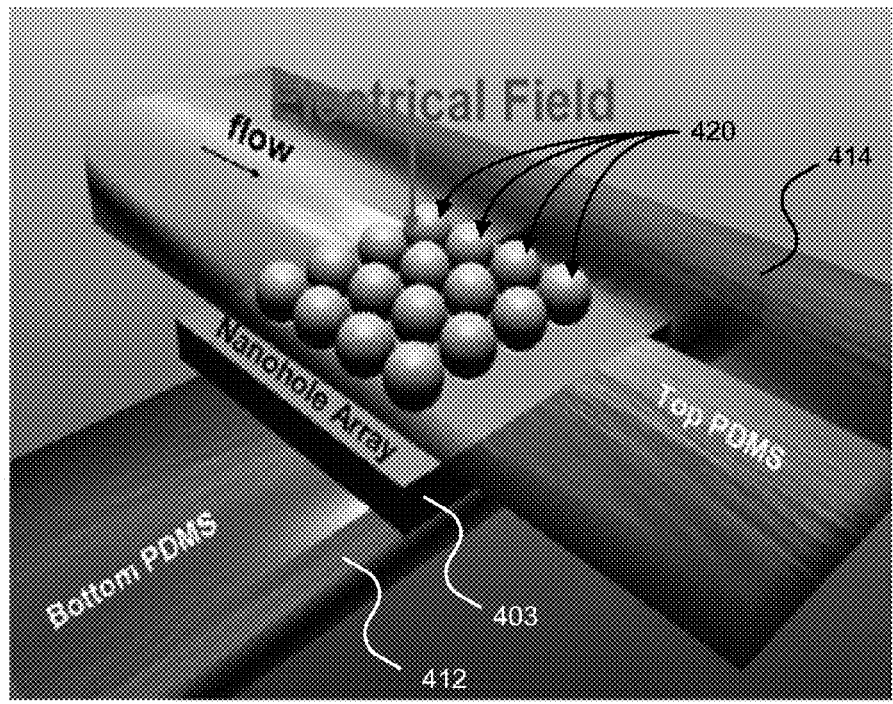

FIGS. 4D and 4E show schematic illustrations of the nanoparticles 420 trapping on the nanochannels 413. As shown in FIG. 4D, the nanoparticles 420 in suspension in the fluid fluidically flow through the microchannel 414. For example, the fluid containing the nanoparticles 420 can be delivered into the nanochip device 400 from the exemplary inlets on the microchannels 414. As shown in FIG. 4E, when an electric field is applied, the nanoparticles 420 are captured onto the underlying membrane having the nanochannels 413 (e.g., defined by the nanohole pattern), connecting the top layer 404 to the bottom layer 402.

The exemplary system integrated with the nanochip device 400 uses electrokinetic forces to control the flow of the nanoparticles 420 onto the nanochannels 413, e.g., rather than pressure gradients, since the fluid speed is largely independent of the channel size for the former while the pressure gradient must increase inversely to the square of channel size to maintain a given flow speed. For example, at the nanoscale, the required pressure gradient becomes so high that leakage becomes problematic for the polymer channels. Moreover, for example, electrokinetic forces can be used to control individual nanoparticles. Both lateral flow (across the individual microchannel) and transverse flow (from the top microchannel 414, through the nanochannel 413, and out of the bottom microchannel 412) can be controlled by changing the direction of the electrostatic field resulting from applying voltages to the different electrodes. The charged ions in the solution will drag the solution through the channels from the inlet to the outlet.

The electrokinetic force used by the integrated system include the use of electroosmotic and electrophoresis flows to manipulate the particle (e.g., nanoparticles, molecules, and/or cells). For example, the electroosmotic flow can be generated from the charged liquids formed closed to the nanochannel wall's surface and the particle's surface, e.g., thereby creating electrical double layers whose polarities are material dependent. The applied electric field displaces the charged liquids in the electrical double layers to generate this electroosmotic flow, driving the particles, molecules, and/or cells in the solution. For example, electrophoresis can be generated as water molecules are dragged along by the charged particles, e.g., which are either propelled or repelled by the electric field depending on the their polarity.

Figure 4F:
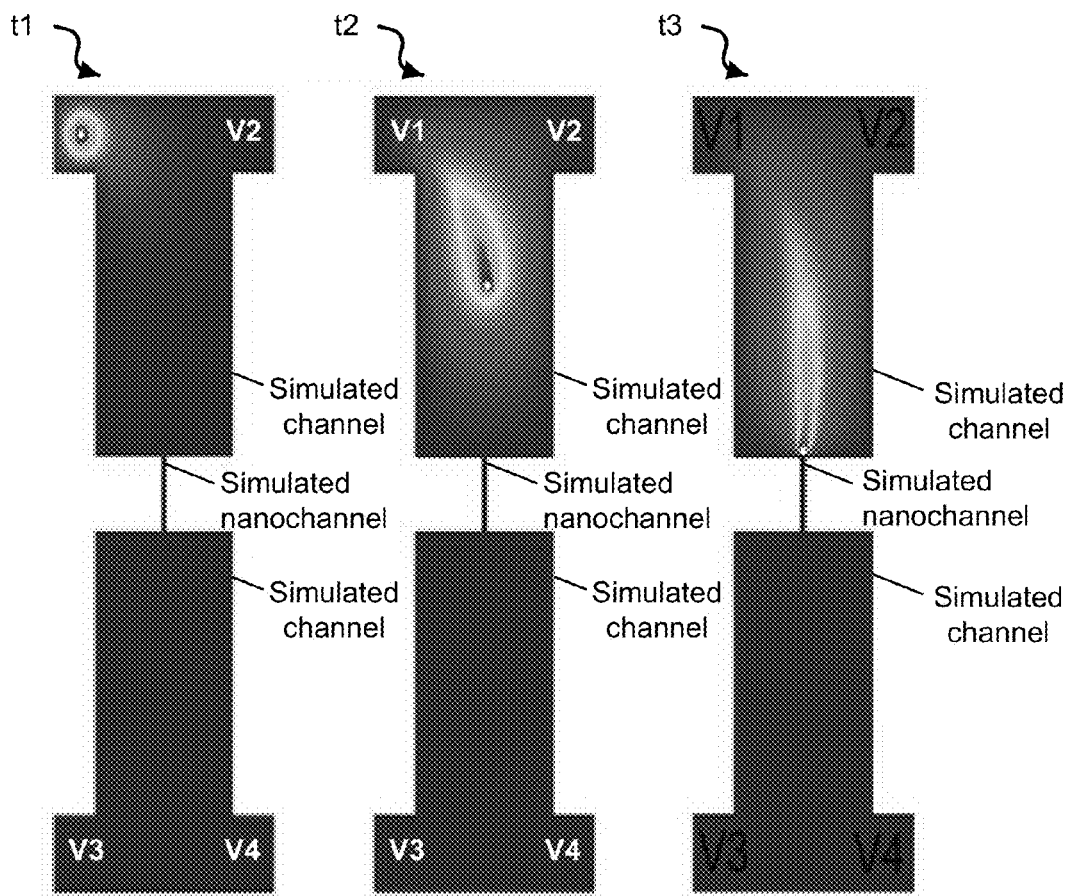
FIG. 4F shows a series of diagrams illustrating a simulated particle flow for a negatively charged nanoparticle.

FIG. 4F shows a series of diagrams illustrating a simulated particle flow for a negatively-charged nanoparticle. The diagram shows a moving mesh finite element method (FEM) simulation of the exemplary negatively-charged nanoparticle in motion in three exemplary stages t1, t2, and t3 when an electric field is applied. In this example, the electrode V4 is connected to a positive voltage, the electrode V1 is grounded, and the electrodes V2 and V3 are disconnected. For example, with the applied electric field to induce 'nanoflow', the nanoparticles are captured onto the opening of the nanochannels and assemble themselves according to the underlying nanochannel pattern, forming a real-time nanophotonic structure. The functionality of the assembled nanophotonic structure depends on the designed nanochannel pattern and its effective index of refraction as determined by the size of the nanochannels, the nanoparticle's properties, such as its index of refraction, and the depth in which the nanoparticles are trapped into the nanochannels. For example, the shifting of the transmission peak can be observed when nanoparticles are captured onto the nanochannels.

Figure 4G:
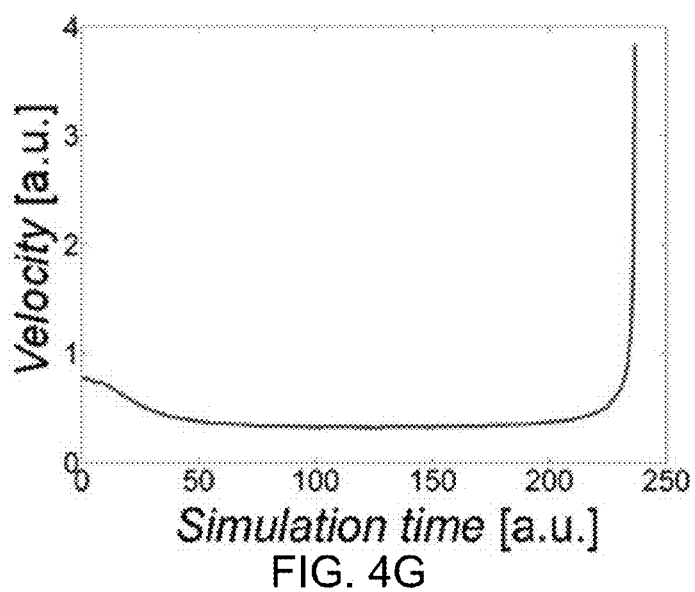
FIG. 4G shows an exemplary plot of the normalized particle velocity versus the simulated time.

FIG. 4G shows an exemplary plot of the normalized (to the unbounded medium) velocity of the particle (e.g., a 200-nm diameter particle) versus the simulated time. For example, as the particle nears the surface of the nanochannel, the velocity increases dramatically as the particle is pulled onto the nanochannel.

For example, to understand the exact behavior of the particle dynamics in the fluid medium, a fluid-particle interaction was simulated. A generalized Galerkin finite element method was used in the exemplary simulation to incorporate both equations of the fluid flow and of the particle motion into a single variational equation, e.g., allowing the hydrodynamic interactions to be eliminated and rendering the explicit evaluation of the hydrodynamic interactions unnecessary. To track the position of the particle, the moving mesh method was used and implemented in the exemplary FEM simulation since the fluid-particle interface is clearly defined at each time step. It considers the relative position of the particle as a boundary of the fluid domain and uses an arbitrary Lagrangian-Eulerian (ALE) technique to create the mesh grid at each time step. The particle surface and its interior are considered as a single entity that moves with the particle. The fluid velocity can be computed using Laplace's equation. In the exemplary simulation, the mesh grid is updated based on the motion of the particle and is checked for element degeneration at each time step. If the detected distortion in the mesh is beyond a pre-defined threshold, a new mesh is generated and the fluid flow fields are projected from the old grid onto the new grid. The exemplary simulations were implemented for a two-dimensional structure with one nanoparticle and one nanochannel to reduce computational complexity.

The exemplary simulations included utilizing a transient model to study the simultaneous translation and rotation of the particle. For example, in order to readily solve the electrophoretic problem, a coordinate transformation was performed. The particle is fixed and its translational velocity after nondimensionalization, $V^*_p$, is transferred to the channel walls. The transient boundary conditions are:

$$v^* = \gamma(I-nn)\cdot\nabla^*\phi^* \text{ on } \Gamma_{wall}, \quad (1)$$

$$v^* = V^*_p + \omega^*_p \times (x^*_p - X^*_p) + (I-nn)\cdot\nabla^*\phi^* \text{ on } \Gamma_{particle}, \quad (2)$$

where $\gamma = \zeta_w/\zeta_p$ is the ratio of the zeta potential of the channel wall to that of the particle, $(I-nn)\cdot\nabla^*\phi^*$ defines the nondimensionalized electric field tangential to the surface where I is the identity tensor and n is the unit vector in the x-direction across the fluidic channel, $V^*_p$ is the nondimensionalized translational velocity of the particle in the x-direction, $\omega^*_p$ is the nondimensionalized rotational velocity, $x^*_p$ is the nondimensionalized position vector of the particle boundary, and $X^*_p$ is the nondimensionalized position vector at the center of the particle.

The system of equations is nondimensionalized using the following exemplary parameters: the particle's radius $\alpha$, the applied electric voltage $\phi_0$, and the electrophoretic velocity of the particle in an unbounded flow defined as $V_\infty = (\in\in_0 \zeta_p/\mu)(\phi_0/\alpha)$, where $\in$ is the dielectric constant of the electrolyte solution, $\in_0$ is the permittivity of vacuum, and $\mu$ is the fluid viscosity. In these exemplary calculations, time is nondimensionalized as $t^* = (V_\infty/\alpha) t$. The fluid velocity v on $\Gamma_{in}$ and $\Gamma_{out}$ (the inlet and outlet) was solved using the coupled Navier-Stokes and electrical DC conductive application modules in the FEM software, with fluid velocity boundary conditions applied on $\Gamma_{wall}$ and $\Gamma_{particle}$.

For each time step, Newton's second law is solved for the translational and rotational velocities using:

$$F^* = \int \sigma^* \cdot n \cdot d\Gamma^*_p = m^* \frac{dV^*_p}{dt^*}, \quad (3)$$

$$T^* = \int (x^*_p - X^*_p) \times (\sigma^* \cdot n) d\Gamma^*_p = I^* \frac{d\omega^*_p}{dt^*}, \quad (4)$$

where $\sigma^*$ is the nondimensionalized stress tensor, $m^*$ is the particle's nondimensionalized mass and $I^*$ is the moment of inertia of the particle.

The exemplary simulations, as shown in FIG. 4F, demonstrated that the particle is manipulated by the applied electric field and is captured onto the nanochannel. For example, the values used in the simulation correspond to following: the radius of the nanoparticle was 100 nm; the radius of the nanochannel ranged from 25 nm to 75 nm; the zeta potentials of the nanoparticle and PDMS are −30 mV and −82 mV, respectively; the density of the fluid and nanoparticle are 1000 kg/m³ and 1050 kg/m³, respectively; and the conductivity of the 10 mM phosphate buffer saline (PBS) solution is 1.59 S/m. For example, a higher molarity of the PBS solution may result in a higher conductivity with a subsequent decrease in the required voltage to control the flow of the nanoparticle. However, for example, for most biological applications, 10 mM PBS (1×PBS) is typically used since a higher molarity may not be biocompatible; therefore, 10 mM was chosen as a baseline for these exemplary simulations. The exemplary simulations and implementations of the disclosed technology can also include using smaller nanoparticles including sizes smaller than 100 nm.

To produce the exemplary nanochip devices such as the device 400 illustrated in FIGS. 4A-4E, a multilayer fabrication process is described, in which the nanochannels of the intermediate layer 403 is sandwiched between the microchannel layers 402 and 404. For example, the microchannel layers 402 and 404 can be made of PDMS polymer material that can be patterned using standard soft lithography with channel widths ranging from 50-150 μm and a channel depth of approximately 40 μm. The nanochannels can be made from a photoresist material, e.g., SU8, through a cost-effective holographic lithography technique, in which the nanochannels are formed by multiple laser exposures. For example, the size of the nanochannels can be controlled by changing the exposure dosages or oblique sputtering after photoresist development. For the multilayer nanochip platform of the disclosed technology, a substantially seamless bond should exist between adjacent layers. PDMS can firmly bond to a Si-based material due to the —Si—O—Si— bond. Since SU8 does not adhere well to PDMS, a silicon dioxide adhesion layer (~2 nm) can first be deposited onto the nanochannel array at an oblique angle. Silicon dioxide can be used since not only does it adhere well to SU8, but also it functions as a dielectric and will not affect the electrostatic fields applied across the layers to control the flow of the nanoparticles.

Figure 5:
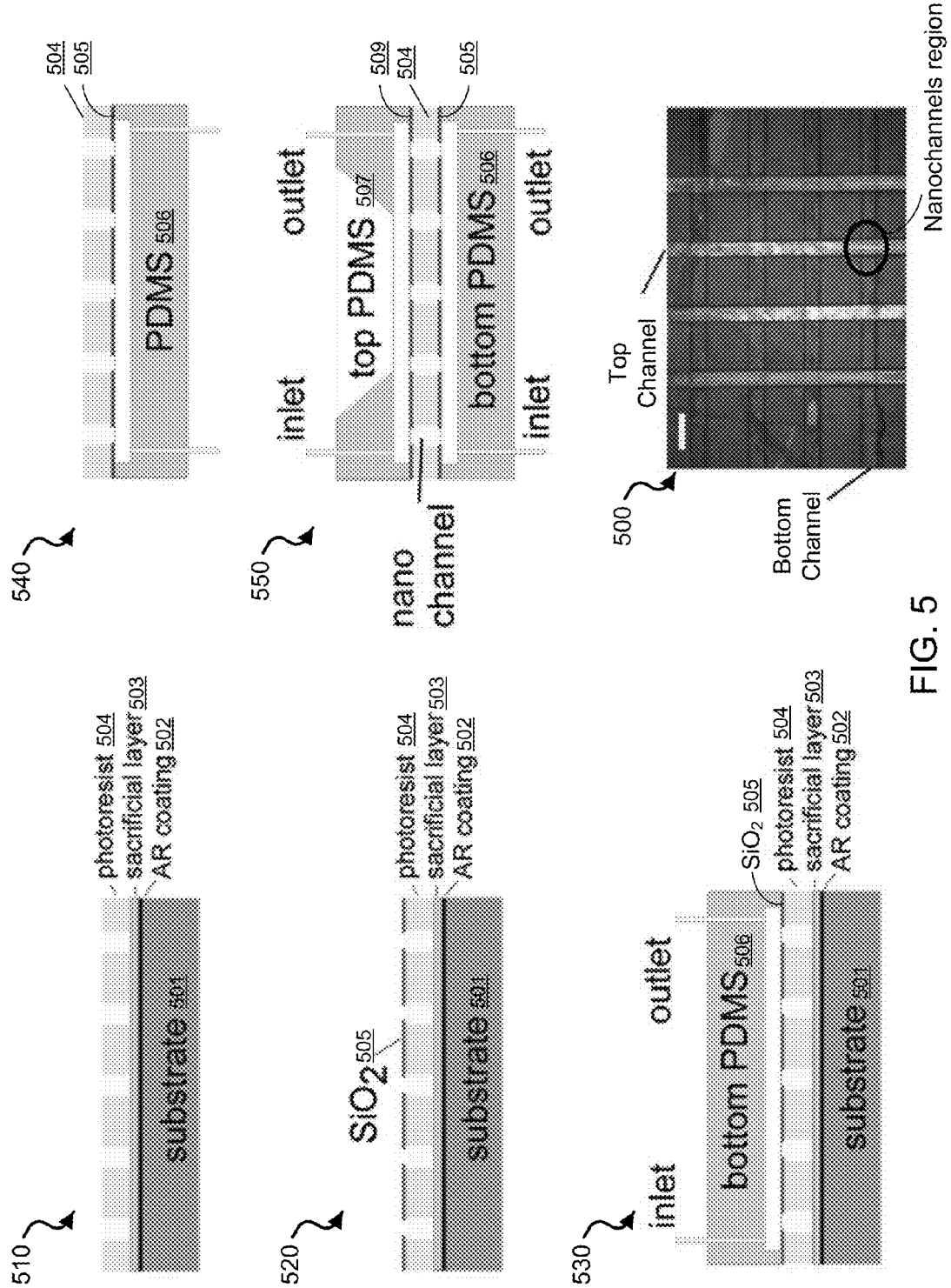
FIG. 5 shows an illustrative process diagram of an exemplary fabrication method to produce exemplary multilayer fluidic nanophotonic and nanoplasmonic characterization nanochip devices of the disclosed technology.

FIG. 5 shows an illustrative process diagram of an exemplary fabrication method to produce exemplary multilayer fluidic nanophotonic and nanoplasmonic nanochip devices of the disclosed technology. The fabrication method includes a process 510 to prepare the substrate and deposit the intermediate layer. The process 510 includes cleaning substrate 501 with piranha solution and subsequently spinning and baking an antireflection (AR) coating 502, a sacrificial layer 503, and an SU8 photoresist layer 504. For example, the nanochannel fabrication process 510 can include spinning the AR coating, the sacrificial layer material, and the SU8 photoresist on a clean microscope slide to serve as the substrate 501 before using holographic interferometric lithography to expose the nanoholes. The nanohole pattern is then exposed. The fabrication method includes a process 520 to deposit an adhesion layer 505 (e.g., a patterned $SiO_2$ adhesion layer) over the photoresist layer 504. For example, $SiO_2$ can be sputtered at an oblique angle as an adhesion layer for the subsequent PDMS layer. The fabrication method includes a process 530 to bond a PDMS material 506 to the $SiO_2$ surface 505 to form the bottom layer including the microfluidic channels. For example, the bottom PDMS layer 506 can be structured to include microfluidic channels that align with the nanochannels of the intermediate layer and include inlet and outlet channels. The fabrication method includes a process 540 to develop the sacrificial layer 503 to release the nanohole pattern from the substrate 501 (e.g., glass substrate) to produce the nanochannel membrane of the intermediate layer, e.g., attached to the bottom layer. In some implementations, for example, the nanochannel membrane can be configured with thickness of 2 µm. The fabrication method includes a process 550 to deposit another adhesion layer 509 (e.g., a patterned $SiO_2$ adhesion layer) on top of the nanochannel membrane surface of the intermediate layer. For example, another $SiO_2$ adhesion layer can be sputtered on the top membrane surface before bonding it to a top layer 507, e.g. of PDMS material, including microfluidic channels that align with the nanoholes. In some implementations, for example, a concave aperture can be made in the top layer 507 capable of fitting a microscope objective in the aperture for microscopy imaging. For example, the top PDMS layer 507 can be made using a multi-step PDMS curing process. The microchannels in the top PDMS layer 507 are aligned orthogonal to the microchannels in the bottom layer, as shown in the image 500 of FIG. 5. In some implementations, for example, the fabrication method can include a process for connecting inlets and outlets of the microfluidic channels to a reservoir or reservoirs, e.g., using electrically conductive needles coupled to the inside of tubes placed in the inlets and outlets. For example, the electrically conductive needles can serve as electrodes of the nanochip device, e.g., electrically coupled to an electrical signal source via conductive wires to supply a voltage at the electrodes. In other implementations, for example, the fabrication method can include directly inserting the electrically conductive wire into the microfluidic channels, e.g., at each end of the channels. As shown in the image 500 of FIG. 5, in the center of the multilayer device, four microchannels (vertical) are configured in the top layer 507 and four microchannels (horizontal) are configured in the bottom layer 506. The circled area denotes a node of this intersection between a top microchannel, the nanochannels in the membrane, and a bottom microchannel. The scale bar shown in the image 500 is 200 µm.

Figure 6A:
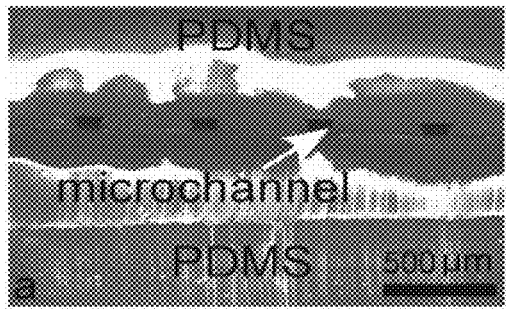
FIGS. 6A-6D show cross-sectional scanning electron microscopy (SEM) images of an exemplary multilayer nanochip.
Figure 6B:
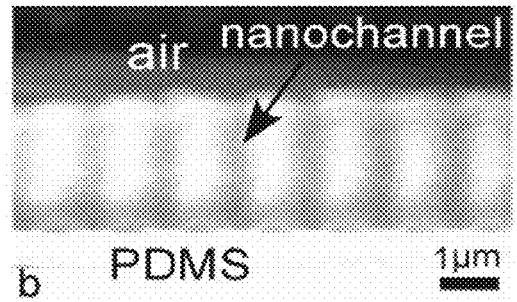
Figure 6C:
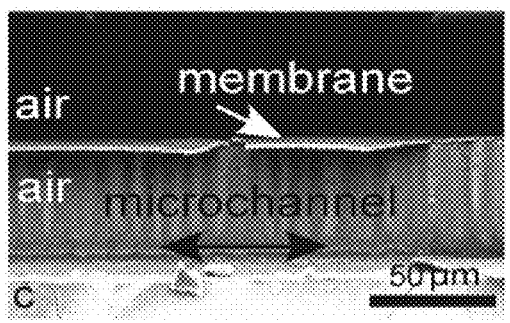
Figure 6D:
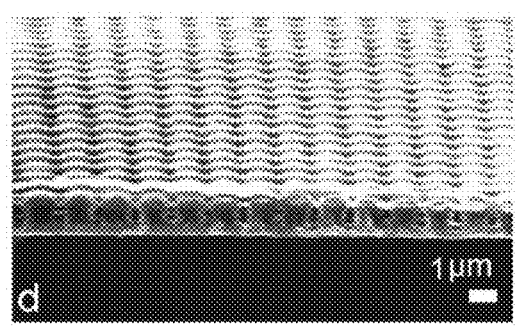

FIGS. 6A-6B show cross-sectional scanning electron microscopy (SEM) images of an exemplary multilayer nanochip fabricated using the described exemplary fabrication method. For example, the cross-sectional SEM images of the exemplary multilayer nanochip were taken after it had been cut in halves to expose the nanochannel membrane connecting the microchannels from the top to the bottom layer. FIG. 6A shows the four microchannels on the top PDMS layer. FIG. 6B shows a close-up of the membrane in one of the microchannel, revealing completely developed nanochannels. FIG. 6C shows one of the bottom horizontal microchannel orthogonal to the four top channels. FIG. 6D shows the suspended nanochannel membrane with its cross-section revealing the nanochannels. The exemplary scale bars shown in FIGS. 6A, 6B, 6C, and 6D are 500 µm, 1 µm, 50 µm, and 1 µm, respectively.

Exemplary implementations of an exemplary nanochip device integrated with the system to provide fluidic flow and applied electric fields were performed. For example, the fabrication method described in FIG. 5 was implemented to produce a multilayer nanophotonic chip device. In this example, a standard microscope glass substrate was cleaved and divided into four smaller pieces and then cleaned using piranha solution at 300° C. for an hour. An antireflection coating (e.g., WiDE-15B, Brewer Science) was then spun at 3000 rpm for 30 s onto the substrate and baked for 30 min at 185° C. SU8-2002 photoresist (from MicroChem) was spun at 3000 rpm for 30 s and baked for 20 min in an oven at 95° C. The exemplary nanohole pattern was then exposed using two-beam interferometric holographic lithography technique. A UV laser beam (e.g., Innova 300, Coherent Corp.) was spatially filtered, expanded, and beam-splitted into two paths. The two identical beams were incident at an angle onto the photoresist-coated substrate, which was mounted onto a computer-controlled piezoelectric stage. The periodicity of the nanohole pattern was determined by the angle of incidence of the two beams and the laser wavelength. Two exposures were implemented to fabricate the exemplary nanohole pattern: the first exposure created a 1-D grating, then the stage was rotated 90 degrees before the second exposure of equal time was implemented to form the exemplary 2-D nanohole pattern. The substrate was post-exposure baked (PEB) for 1 min at 95° C. and then developed with SU-8 developer (from MicroChem) for 3 min. The nanohole size was determined by the exposure time as well as the development time. $SiO_2$ was then subsequently sputtered as an adhesion layer at an oblique angle using the RF cathode of Discovery 18 (from Denton Vacuum) as the stage was rotated. The surface was then bonded to the bottom PDMS chamber. MF319 developer solution (obtained from Shipley) was used to remove the exemplary sacrificial Omnicoat layer (from MicroChem) from the glass substrate to form the nanochannel membrane.

Figure 7A:
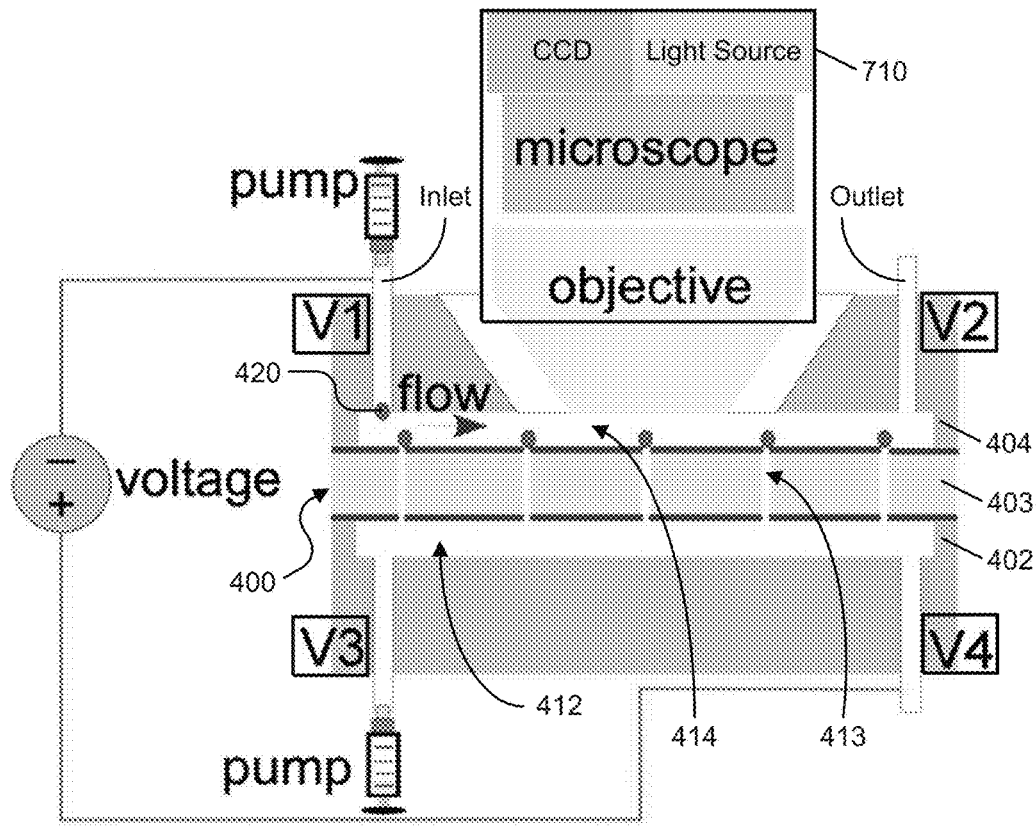
FIGS. 7A-7C show schematic diagrams and images of an exemplary setup of an exemplary multilayer nanophotonic chip device integrated with a fluidic-electronic system.
Figure 7B:
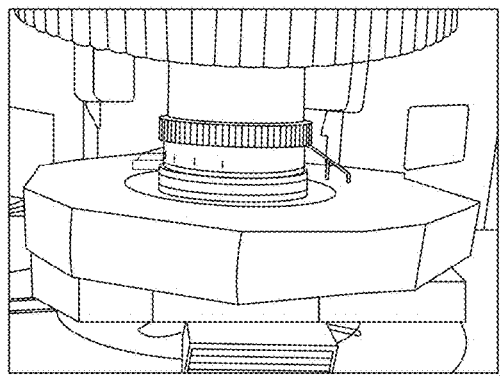
Figure 7C:
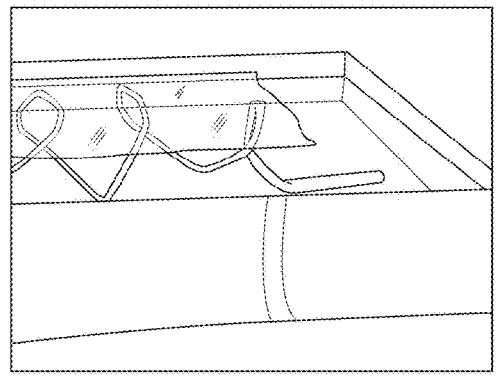

FIG. 7A shows schematic diagram of an exemplary setup of the multilayer nanophotonic chip device 400 integrated with the fluidic-electronic system (shown in FIG. 4C) to provide fluidic flow of nanoparticles in a fluid and an applied electric field to trap the nanoparticles on the nanochannels 413 of the nanochip device 400. The exemplary setup of the integrated system included using syringe pumps initially to establish microflow of the fluid containing the nanoparticles through the microchannels of the nanochip device 400 and using an electrical signal source to switch the voltage control for nanoflow. In the exemplary setup configuration of the system, the microscope objective fits inside a concave aperture formed in the top PDMS layer, e.g., in which the thickness at the center was configured to be within a 40× objective lens' working distance, as shown in the image of FIG. 7B. FIG. 7C shows an image of the exemplary nanochannel membrane after it has been transferred onto the bottom PDMS chamber. In some implementations, for example, the system can include an optical module 710 that is coupled to supply light to the nanophotonic chip device 400. For example, the optical module 710 can provide incoherent (white) light to the nanophotonic chip device 400 to enable optical imaging of the captured substances (e.g., particles or cells) on the exemplary nanoscale resonant structures (e.g., nanochannels 413). Also, for example, the optical module 710 can be used to effectuate an optical trapping force to trap a molecule or particle at one end of a nanochannel or within the nanochannel, e.g., which can be implemented without or in compilation with the applied electric field by the electric signal module electrically coupled to the electrodes of the nanophotonic chip device 400. In some implementations, for example, the optical module 710 can provide coherent light, e.g., including a laser that emits light at a desired wavelength (e.g., 785 nm) to the nanophotonic chip device 400 for optical interrogation of the nanophotonic chip device 400. For example, the optical module 710 can direct a coherent light beam on the nanochip device 400 and detect inelastic scattering of the light beam by at least some of the trapped particles at the openings of the nanochannels 413 to determine their Raman spectra, in which the exemplary resonant nanostructures amplify detected signals corresponding to the inelastic scattering.

The exemplary implementations of the exemplary multilayer nanophotonic chip device with the system to provide fluidic flow and applied electric fields included monitoring the device under a microscope with the exemplary 40× objective. In this exemplary implementation, fluorescent beads were used as the exemplary nanoparticles for ease of observation. For example, 2-μm and 1-μm polystyrene beads (Duke Scientific) and 200-nm carboxylated fluorescent beads (e.g., FluoSpheres, Life Technologies) were used. For example, a low concentrations of exemplary beads (e.g., $2.285 \times 10^9$ particles/mL of 10 mM phosphate buffered saline (PBS) solution, pH level of 7.0) were used during the exemplary implementation. Initially, for example, a nanoparticle solution and PBS solution were flown into the inlets of the top and bottom PDMS chamber layers, respectively, e.g., using electrical syringe pumps (Nanojet N5000, Chemyx Corp.). For example, the pressure difference between the top and bottom microchannels was kept the same to ensure that no significant pressure was applied on the nanochannel membrane to prevent membrane deformation. First, large bead (~1-2 μm) solution was introduced into the top microfluidic chamber and monitored via a CCD camera to check the integrity of the multilayer platform. The flow rate was set such that a single particle flow could be observed with a 40× microscope objective by adjusting the pumping pressure. For example, after confirming the integrity of the multilayer platform, pressure pumping was replaced with voltage control on the inlets and outlets for both lateral and transverse flow by adjusting the voltage potential between the inlet and the outlet, e.g., V1 versus V2 and V3 versus V4. After the liquids flowed out of the outlets, voltage control was switched using two electrodes V1 and V4 connected diagonally across the top and the bottom chamber, as shown in FIG. 7A. In the exemplary implementations, a DC voltage of 3-20 V was utilized for different flow rates. In other implementations, ac voltage may be applied, e.g., with or without a DC signal. For example, nanoflow was generated by applying a voltage between the inlet on the top channel (V1) and the outlet on the bottom channel (V4). The microparticles were observed to have slowed down, captured onto the nanochannel membrane, or released from the membrane by adjusting the strength of the voltage potential. Then, the reservoir connected to the top microchannel was changed to the exemplary fluorescent 200-nm-diameter nanoparticle solution. The exemplary nanoparticles' motion was captured using a high-speed camera (e.g., iXon, Andor Corp.). The exemplary fluorescent bead nanoparticles were excited using an Argon laser (e.g., Innova 70, Coherent Corp.) under transmission mode. A long-pass filter (e.g., HQ545LP, Chroma Corp.) was used in the microscope turret to allow only the fluorescent emission wavelength to reach the camera. Although negative charged particles were used in the experiment, positive charged particles could easily have been used. The only change would be reversing the polarity of the electrodes. Although the index contrast may be low between polystyrene nanoparticles and the SU8 photoresist, it can still yield useful functionality. It is noted that various materials of nanoparticles can be implemented (e.g., Si and Au), and depending on the particular application, one can select materials with proper indexes to achieve the desired functionality.

The exemplary implementations included evaluating the real-time manipulation of these exemplary nanoparticles by high-resolution imaging of the manipulated nanoparticle pattern. In this example, the exemplary multilayer nanophotonic chip device was dismantled from the system while keeping the trapped nanoparticle pattern intact. For example, the removal process can include slightly increasing the pumping pressure in the top microchannel while maintaining the voltage between V1 and V4 until all the solution in the reservoir is out of the top channel outlet. Then the inlets and outlets can be disconnected, and the top PDMS layer can be carefully peeled off. For SEM high-resolution imaging, for example, gold can be sputtered onto the nanochannel membrane with the trapped nanoparticles prior to SEM imaging.

Figures 8A, 8B:
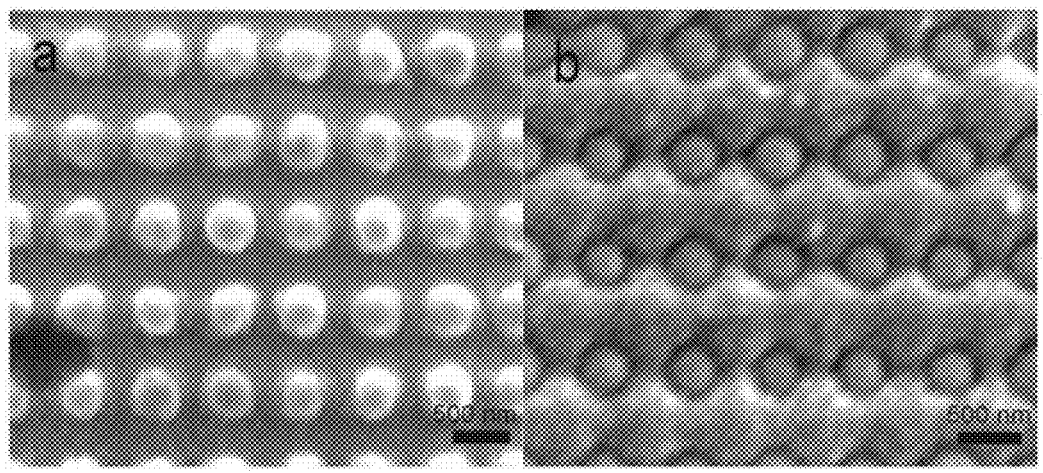
FIGS. 8A and 8B show high-resolution SEM images of the exemplary nanoparticles captured onto an underlying nanochannel array.

FIG. 8A shows an SEM image of the exemplary 200-nm nanoparticles that were captured onto the underlying 600-nm-pitch nanochannel array after the voltage was applied to form this exemplary 2-D nanophotonic nanoparticle array. The size of the nanochannels was configured to be approximately 50 nm, e.g., and thus the nanoparticles were configured on the surface of the nanochannels. FIG. 8B shows an SEM image depicting the size of the exemplary nanochannels to be approximately 150 nm, and thus the exemplary 200-nm nanoparticles were configured to be mostly (trapped) inside the nanochannels. The exemplary scale bars of FIGS. 8A and 8B are 500 nm. Consequently, for example, the effective index is different for these two exemplary nanoparticle array. Analogous to the design of photonic crystal structure with defect states to tailor the effective index to produce photonic bandgap, the same concept can be applied in designing complex nanoparticle structures. This exemplary implementation demonstrates an example of the disclosed multilayer, nanophotonic chip approach in an aqueous environment, whose properties (e.g., transmission peak, effective index) can change depending on the underlying nanochannel pattern, the size and the number of nanoparticles or biomolecules, and their refractive indices. The real-time manipulation of the nanoparticles on the nanochannel array can be effected based on the control of the nanoflow of the nanoparticle-containing fluid into the nanochannel with the applied electric field and the microflow into the microchannels with pressure gradient.

The disclosed process to produce a multilayer, nanofluidic platform for real-time manipulation and assembly of nanophotonic structure was demonstrated in the described exemplary implementations. For example, electrokinetic forces were employed to induce nanoflow in the nanochannel of the suspended membrane to self-align nanoparticles onto the underlying nanochannel pattern. Exemplary 200-nm nanoparticles were manipulated and captured to form an exemplary 2-D nanoparticle array, e.g., with 600-nm periodicity. The size of the exemplary nanochannel can affect what percentage of the nanoparticle's surface area is inside the nanochannel and, thus, can affect the effective refractive index of the structure. The disclosed techniques can be extended to control individual nanoparticles, biomolecules, and/or quantum dots on simple or complex nanochannel designs and/or electrode patterns to form functional nanophotonic and nanoplasmonic structures and devices. Thus, the disclosed technology can be used to monitor and control nanostructures in an aqueous, biocompatible environment in real time and in vivo, e.g., for applications ranging from targeted drug delivery to construction of nanophotonic devices. The disclosed techniques described here can also be used to design other functional patterns such as plasmonic nanoparticle clusters for tailored electric and magnetic resonances, efficient nano-lenses with progressively decreasing nanosphere size and separation, 1-D nanoparticle structures for biosensing and electromagnetic propagation applications, and individually addressable nanoparticle array, among others.

In another aspect, the disclosed technology includes systems, devices, and methods to produce nanocrescent-like structures, referred to as nanotorch structures.

In some implementations, for example, the disclosed nanotorch structures can function as a surface enhanced Raman scattering (SERS) structure because, instead of relying on a few nanometer gap inter-particle plasmonic coupling to achieve local field enhancement, intra-particle plasmonic coupling between the cavity modes and the tip edges are utilized to achieve high local field enhancement at the tips. Fabrication processes are disclosed to produce the nanotorch structures with controllable cavity rim opening and deterministic orientation, e.g., which can be used to yield uniform Raman measurements, including three dimensional (3-D) upright oriented nanocrescent structures resting on nanopillars or substrate. Each structure can serve as a single SERS substrate, which can greatly reduce background noise in Raman characterizations. The disclosed nanotorch structures with a smaller rim opening can provide higher enhancement factors results, e.g., as compared to nanostructures with larger openings.

Surface enhanced Raman scattering (SERS) detection has gradually become a powerful tool from material identification to single molecule detection. However, conventional fabrication methods of SERS substrates still include functional challenges based on unsolved issues to be capable of producing commercialized SERS substrate devices, e.g., such as achieving high local field enhancement (LFE) while simultaneously giving high repeatability. Previously, nanoparticles were first used as a SERS substrate, but were soon replaced by nanoparticle assemblies because of the former's low local LFE and the latter's higher LFE due to coupling between particles. Yet, this improvement came at a cost, since the random locations of the hot spots made the substrate impossible for quantitative analysis of the reagents. Other approaches included electron beam lithography and focused ion beam to fabricate finely defined nanostructures, e.g., such as the bowtie structures for high LFE at the tips, but are limited by high cost and planar methodologies that prohibit successful commercialization of such techniques and devices. Some systems include multiple resonance coupling of nanocrescent or half-shell structures, in which the coupling among tip-to-tip, tip-to-cavity, cavity-to-body are involved, of the ring and disc structure, where coupled multiple dipoles are involved, and of the composite nanocrescent and disc structure, where dipole to quadruple coupling are involved. Some existing nanocrescent structures have been used as SERS substrate devices, e.g., based on their optically tunable anisotropic metal nanostructure. For example, unlike structures that rely on a few nanometer gap inter-particle plasmonic coupling to achieve high local field enhancement, nanocrescent structures can be fabricated from relatively large sacrificial nanoparticles with diameter of a few hundred nanometers. The plasmonic resonance can be tuned by choosing a different nanoparticle size. Currently, existing nanocrescent structures are two-dimensional (2D) nanocrescents and have been shown to localize the field to a smaller volume by decreasing the tip distance, which therefore increases the value of its complex amplitude. However, such field localization and enhancement using 2D nanocrescent structures cannot be used to fully realize other types of coupling, especially the tip-to-tip coupling, which involves a small gap.

The disclosed nanotorch structures are configured to include smaller tip-to-tip spacing (in 3D, smaller rim diameter) to yield higher local field enhancement. Furthermore, disclosed nanotorch structures are configured to be upright on their carrier substrate with controllable rim diameter and deterministic orientation. The disclosed nanotorch structures can be implemented in a variety of molecular sensing and/or biosensing applications, e.g., because they induce the maximum LFE for normal photon incidence and yield repeatable Raman measurement with less than 20% standard deviation. For example, each individual nanotorch structure can serve as a single SERS substrate. The disclosed nanotorch structures can thus provide repeatability of SERS measurements for the limit of detection, as well as for the spatial resolution.

Figure 9A:
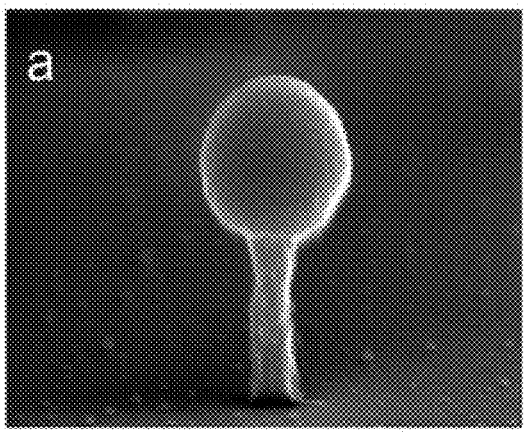
FIGS. 9A-9D show SEM images of an exemplary nanocrescent and nanotorch structures of the disclosed technology.
Figure 9B:
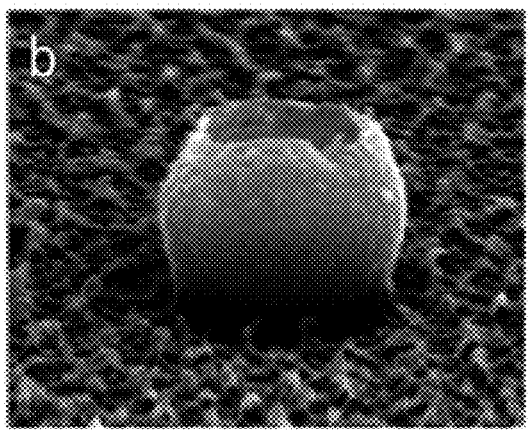
Figure 9C:
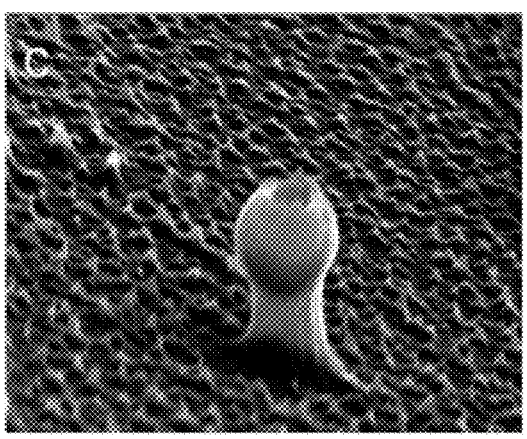
Figure 9D:
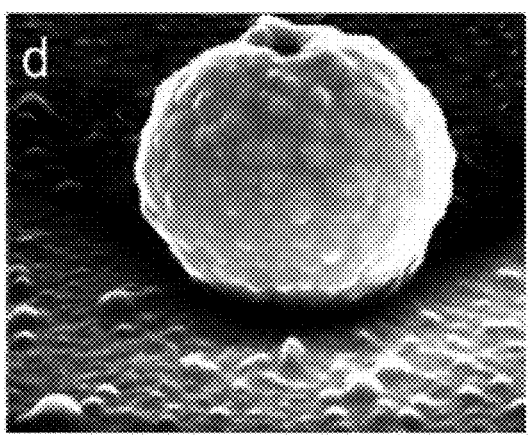

FIG. 9A shows an SEM image of an exemplary nanopillar pedestal to host an exemplary nanotorch structure. FIG. 9B shows an SEM image of an exemplary upright nanocrescent structure with larger rim opening (e.g., ~260 nm), which can be fabricated using the disclosed techniques. FIG. 9C shows an SEM image of an exemplary upright nanotorch structure of the disclosed technology including a smaller rim opening (e.g., ~140 nm) than the exemplary nanocrescent structure of FIG. 9B, which was fabricated using the disclosed fabrication techniques. FIG. 9D shows an SEM image of an even smaller rim opening (e.g., ~50 nm) of the exemplary nanotorch structure. The exemplary images of FIGS. 9A-9D were taken by rotating sample 80 degree to its side.

Exemplary implementations of the disclosed nanotorch structures are described herein, which include exemplary finite element simulations, fabrication techniques, and SERS detection implementations.

An exemplary finite element, full 3D model simulation of the nanotorch structure was implemented, e.g., in finite element method (FEM) using COMSOL Multiphysics. For example, the time-harmonic Maxwell equations of the 3-D model can be solved over the domain of interest, which reduce to the Helmoholtz equations. Low-reflection, absorptive perfectly matched layers (PMLs) were applied on the exterior layers to eliminate non-physical reflections at the boundaries. The scattering boundary condition was used for the incident electric field with a magnitude of 1 V/m polarized along the x-direction. Adaptive meshing was employed to automatically reduce the mesh element size near geometric edges that are rapidly changing within the structure until the maximum field converged. The reported wavelength-dependent refractive index of bulk gold was used. For example, the enhancement factor was calculated from the amplitude ratio of the near-field of the nanotorch and the incident electric field, where the highest value occurs on the rim. Symmetry plane was used in the simulation to reduce the computation time.

Figure 10A:
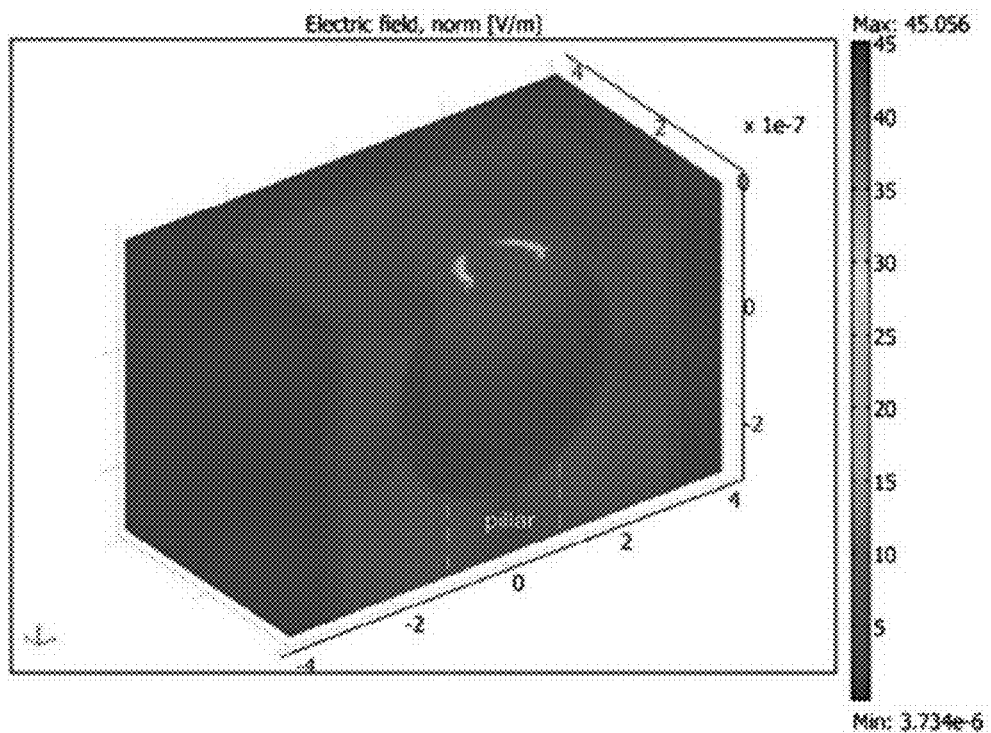
FIGS. 10A and 10B show exemplary 3D FEM simulation plots of exemplary nanotorch structures.

FIG. 10A shows an exemplary 3D FEM simulation plot of an exemplary nanotorch structure comprising of a 100-nm thick nanocrescent on top of a 200-nm pillar. As shown in FIG. 10A, only half of the nanotorch is shown to better reveal the cross-section of the rim and the nanotorch shape. In this exemplary simulation, the exemplary nanotorch is composed of a nanocrescent structure on top of a pillar with a refractive index of 1.47. A planar nanocrescent geometry is formed by subtracting an inner circle with a 150-nm radius, offset from the center by 50.5 nm, from an outer circle with a 200-nm radius, yielding a nanocrescent with a thickness of ~100 nm. A fillet with a radius of curvature of 1 nm was used on the tip of the exemplary nanocrescent to better represent the fabricated structure. For example, a 200-nm-diameter pillar with a height of 200 nm was added below the planar nanocrescent. The exemplary 2D composite structure was then revolved 360 degree around the z-axis to form the 3D nanotorch structure with a rim opening of 140 nm. For example, in the exemplary simulation, the rim opening was 140 nm with a maximum electric field of 45 V/m.

Figure 10B:
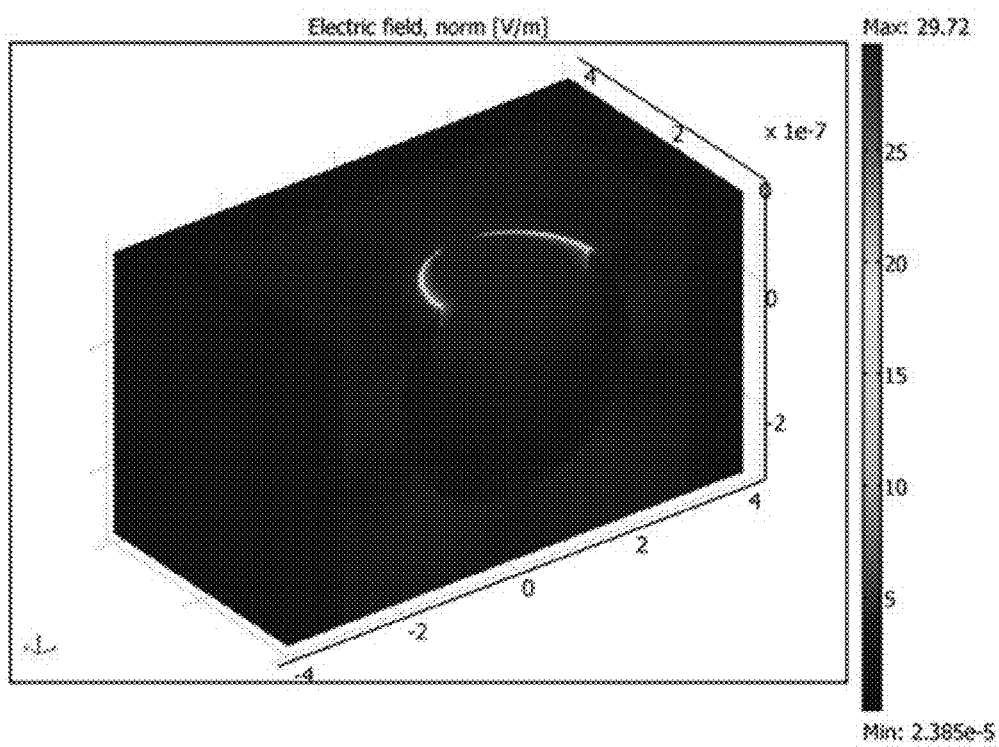

The plasmon resonance can be significantly tuned by varying the cavity offset of the inner dielectric sphere (e.g., air in the exemplary simulation). Changing the offset can invariably affect the rim diameter and the thickness. For example, in planar 2D nanocrescent structures, this translates to tip-to-tip distance and as the offset decreases, the dipole-like coupling increases between the tip, e.g., resulting in increased resonance. For the exemplary 3D nanotorch simulations, the offset and thickness were kept constant. To introduce larger rim opening, the planar nanocrescent was truncated before the 360 degree revolution in the exemplary model. The same 150-nm and 200-nm radii circles were used with the same offset. For example, the planar structure was truncated to create an opening of 130 nm (in radius) and then 1 nm fillet was performed at the tip. After 360 degree revolution, a 3-D nanotorch with a rim opening of 260 nm was simulated using adaptive meshing. For the first case of a nanotorch with a rim opening of 140 nm (as shown in FIG. 10A), a maximum electric field of 45 V/m at the rim was achieved with a total 398,069 meshing elements. This is in contrast, for example, to a lower value of 29 V/m for the 260 nm opening with 607,327 meshing elements (as shown in FIG. 10B). For example, the 260-nm opening has a smaller amplitude compare to the 140-nm opening due to less plasmonic coupling between the cavity and the edges. Also, for example, for different nanotorch sizes, it is shown that the resonance peak is red-shifted as the size increases and the resonance is broaden, which is consistent with the size-effect seen in gold nanoparticles. The exemplary simulations showed that the nanotorch and the nanocrescent can behave similarly in terms of the location and the magnitude of the maximum electric field being concentrated on the rim of structure. Yet, the maximum near-field increases significantly as the fillet decreases, e.g., especially below 1 nm. Increasing the sharpness of the tip (rim) can increase the lightning rod effect, but has little effect on the dipole-like coupling between the tips and cavity. For example, for a fillet radius of 0.25 nm and a correspondingly smaller rim diameter of 72 nm, the total adaptive meshing element count is greater than 700K elements with a maximum electric field greater than 500 V/m. Decreasing the rim opening can produce a red-shift but varying the fillet radius does not significantly change the plasmon resonance wavelength.

Figure 11A:
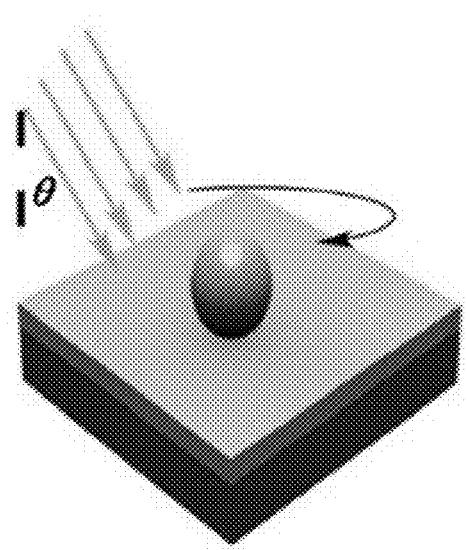
FIGS. 11A-11D show diagrams of exemplary metal deposition setups for fabrication techniques of the disclosed technology to produce nanocrescent and nanotorch structures.
Figure 11B:
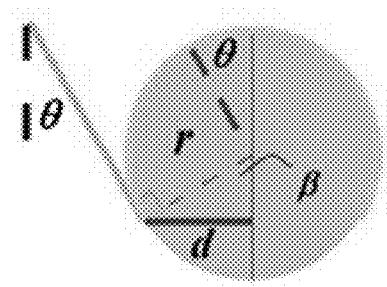
Figure 11C:
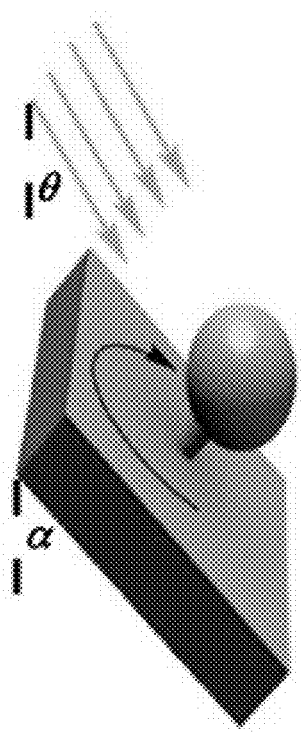
Figure 11D:
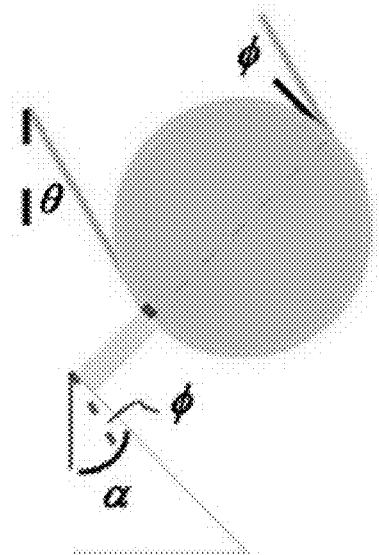

Exemplary fabrications of the disclosed nanotorches are described. FIGS. 11A-11D show diagrams of exemplary metal deposition setups for fabrication techniques of the disclosed technology to produce nanocrescent and nanotorch structures. FIG. 11A shows a diagram of an exemplary metal deposition setup for previously demonstrated fabrication of nanocrescent with large rim opening. FIG. 11B shows a geometrical schematic of the traditional nanocrescent fabrication method with the opening given by length 2d. FIG. 11C shows a diagram of an exemplary metal deposition setup with a nanoparticle sitting on a pillar pedestal mounted on a goniometer for fabricating nanotorch structure with controllable rim opening. FIG. 11D shows a geometric schematic of an exemplary modified deposition process where the opening is determined by the diameter of the pillar.

As shown in FIGS. 11A-11D, two exemplary sputtering setups are analyzed for sputtering processes using an RF sputtering machine. The first example is analogous to conventional setups, except that the substrate was placed on a horizontal rotating stage below the sputtering cathode at an angle of θ~30 degree, as shown in FIG. 11A. The opening of the nanocrescent is calculated to be d=r·(sin β), as shown in FIG. 11B, where for 150-nm-radius nanoparticle and β of 60 degree, the rim opening is 2d=260 nm. In this exemplary setup, the nanoparticles rest on top of a horizontal planar surface and because of the shadowing effect of the sputtering cathode onto the nanoparticles, it is not possible to fabricate nanocrescent with smaller rim opening. The second fabrication setup example is shown in FIG. 11C with the nanoparticles resting on nanopillars. The exemplary substrate is secured on a rotating plate mounted onto a motor that is secured onto a goniometer to control the relative angle of incidence between sputtering cathode and the rotating stage. In this exemplary setup, the goniometer is initially set to 45° so the entire surface area of the nanoparticles is coated with gold except for the small portion that is in contact with the nanopillars. For example, the rim opening is dependent on the diameter of the nanopillar as long as the angle α is larger than θ, as shown in FIG. 11D, e.g., φ=α−θ is greater than zero degree. For example, by changing the goniometer angle, α, the φ angle is altered, which can affect the shape of the nanostructure. For φ=0, for example, nanoring-like structures can be achieved.

Figure 12:
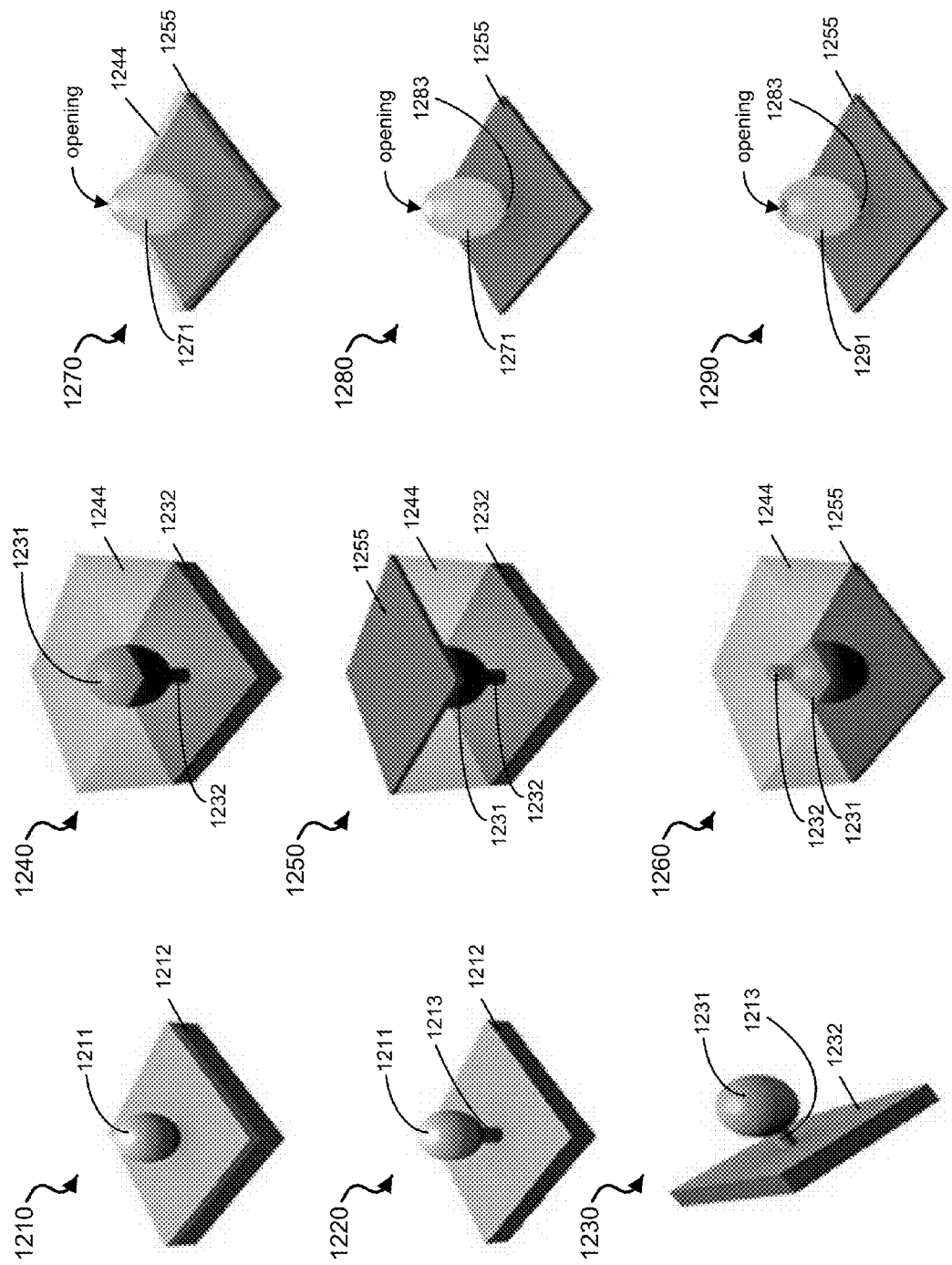
FIG. 12 shows an illustrative process diagram of an exemplary fabrication method of the disclosed technology to produce nanotorch structures.

FIG. 12 shows an illustrative process diagram of an exemplary fabrication method of the disclosed technology to produce nanotorch structures. The fabrication method includes a process 1210 to deposit nanoparticles (e.g. of a sacrificial nanoparticle material, like silica) on a substrate, e.g. as illustrated in the diagram showing an exemplary silica nanoparticle 1211 on an exemplary photoresist-coated BK7 substrate 1212. The fabrication method includes a process 1220 to etch a nanopillar structure between the nanoparticle and the substrate, e.g., as illustrated in the diagram showing the silica nanoparticle 1211 including a nanopillar structure 1213 between the particle and the photoresist-coated substrate 1212. For example, the process 1220 can include reactive ion etching (RIE) of the nanoparticle 1211 to create the nanopillar 1213 that can be used to fabricate nanotorch with small rim diameter opening. The fabrication method includes a process 1230 to sputter the nanoparticle hoisted by the nanopillar on the substrate, e.g., as illustrated in the diagram showing the metal-sputtered nanoparticle 1231 over the nanopillar 1213 on the sputtered substrate 1232. For example, the process 1230 can include implementing an oblique metal sputtering process using the exemplary setup as shown in FIG. 11C. The fabrication method includes a process 1240 to embed the sputtered nanoparticle in an exemplary monomer material, e.g., as illustrated in the diagram showing the nanoparticle 1232 embedded within an exemplary ethoxylated trimethylolpropane triacrylate (ETPTA) monomer 1244. The fabrication method includes a process 1250 to bind the exemplary embedded nanoparticle to an exemplary silicon substrate, e.g., as illustrated in the diagram showing a silicon substrate 1255 coupled to the monomer 1244 that embeds the nanoparticle 1232. The fabrication method includes a process 1260 to remove the substrate 1232, e.g., as illustrated in the diagram showing the embedded nanoparticle 1231 in the monomer 1244 attached to the silicon substrate 1255. For example, the process 1260 can include peeling off the substrate 1232. In some implementations of the process 1260, both the substrates 1255 and 1232 can be removed and a clean substrate can be attached to the monomer-embedded nanoparticle. The fabrication method includes a process 1270 to etch the monomer embedment structure to form a nanocrescent structure, e.g., as illustrated in the diagram showing the exemplary ETPTA monomer 1244 etched down to expose the nanoparticle and etch an opening forming the nanocrescent structure 1271. For example, the process 1270 can include implementing an exemplary RIE etching process to etch ETPTA down to the exemplary nanoparticle to create the nanocrescent structure 1271, e.g., which includes an opening in its sputtered metallic shell exposing the exemplary silica nanoparticle sacrificial material. The fabrication method can include a process 1280 to etch the monomer embedment structure to form a nanopillar structure between the nanocrescent structure and its substrate. The process 1280 is illustrated in the diagram showing the nanocrescent structure 1271 residing on a nanopillar 1283 over the substrate 1255. The fabrication method can include a process 1290 to dissolve the sacrificial nanoparticle material to form the nanotorch structure of the disclosed technology, e.g., as illustrated in the diagram showing the exemplary silica sacrificial nanoparticle dissolved away with the produced nanotorch structure 1291 residing on the nanopillar 1283 over the substrate 1255.

Exemplary implementations of the disclosed fabrication method to produce nanotorch structures were implemented. In this example, silica nanoparticles were used as sacrificial templates for fabricating these upright nanotorches. For example, the nanoparticle solution was diluted to ensure isolated nanoparticles, e.g., in order to analyze the SERS effect on an individual nanotorch, as close-packed nanoparticles may create shadowing effect from neighboring particles and prevent fabrication of nanotorch with small rim diameter. For example, 310 nm silica nanoparticles were made into 0.002% solution in 18 MΩ purified water with a 0.001% of surfactant (e.g., Tween 20) to prevent coagulation. BK7 microscope slides were diced, cleaned with piranha solution and DI water, and then dried with nitrogen. Subsequently, poly-(methyl methacrylate) (PMMA) photoresist was spun onto a cleaned microscope slide substrate (or silicon substrate) and baked. For example, PMMA A4 was spun at 4000 rpm for 45 sec onto the sample substrate and baked for 1 min at 180 degree on a hotplate. The sample was then dipped vertically into the exemplary silica nanoparticle solution (e.g., for 30 sec) and then brought up slowly. As water molecules evaporate from the surface, randomly distributed and isolated nanoparticles were dispersed onto the substrate. In the exemplary implementation of the fabrication process, the samples were then mounted onto an exemplary custom-made rotating stage which was secured onto a goniometer stage. Reactive ion etching (RIE) was then used to create nanopillars, in which the silica nanoparticles act as etching mask. For example, the girth of the nanopillar can be adjusted by adjusting the etching condition, as shown in FIG. 9A. For example, the nanopillar can be used to subsequently dictate the opening of the nanotorch together with the exemplary sputtering setup. In this example, an adhesion layer of chromium (e.g., ~1 nm) was then sputtered onto the nanoparticles with a goniometer angle ($\alpha$) of 45 degree. Subsequently, gold was sputtered to configure a thickness of 100 nm on to the chromium-adhesion layer using RF sputtering cathode. Another layer of chromium (e.g., ~2 nm) was then sputtered to protect the gold material during a later RIE etch process to create the nanotorch pillar. Ethoxylated trimethylolpropane triacrylate (ETPTA) monomer was then mixed with 20% photoinitiator (e.g., (2-hydroxy-2-methyl-1-phenyl-1-propanone) photoinitiator) and then spun onto the exemplary metal-coated silica nanoparticles and slowly ramped up to embed the nanoparticles inside this monomer layer. The sample was then polymerized with an UV light source. A clean silicon substrate was then primed with (3-acryloxypropyl) trichlorosilane (APTCS) and rinsed with ethanol for adhesion to the nanoparticle-embedded ETPTA sample. The two pieces were bind and then baked on a hot plate (e.g., at 60 degree for 30 min) before peeling the two pieces apart. After transferring to the silicon substrate, chromium and gold wet etchants were used to remove the metals on the surface of the monomer. The metals on the nanoparticles were protected from this wet etching process since they are embedded inside the monomer. The sample was then RIE etched again (e.g., at 100 W with 40 sccm of $O_2$, 40 mTorr for 90 sec) to remove the ETPTA layer down to the nanoparticle-level to create the exemplary nanocrescents. To create the nanotorches, for example, the etching time can be prolonged to form the nanopillars. In this example, the sample was dipped and agitated lightly in a 4% diluted HF solution (e.g., 10 mL of HF (49% concentration) in 250 mL of DI water, for approximately 3 min) to dissolve the silica nanoparticles to produce the exemplary nanotorch structures. Also, for example, before SERS characterization, chromium wet etching was done again to remove chromium from the nanotorch structure and expose gold to analyte adsorption. For example, the substrates were treated with 5 mM of benzenethiol in 200-proof bioagent grade ethanol for 3 hr and then rinsed copiously with ethanol 3 times and then carefully dried with nitrogen. The exemplary implementation of the described fabrication process produced upright-oriented nanocrescents and nanotorches with large rim openings, as exemplified in FIGS. 9A-9D.

Exemplary implementations included performing surface enhanced Raman scattering measurement using the exemplary nanotorch structures. For example, a near infrared (NIR) 785 nm laser was used, e.g., because it better matched the scattering resonance of the exemplary nanotorch structures, as well as it can avoid the fluorescence from biomolecules. Additionally, for example, the exemplary NIR laser can provide a deeper penetration depth in biological issues, and the low photon energy minimizes photothermal damage to biomolecules and cells. Moreover, by using a NIR source, it ensures that the detected SERS signal is from the nanotorch and not from a residual nanoparticle, since a NIR source can hardly excite the plasmon resonance in the nanoparticle, which is a necessary condition for the effective near-field energy transfer to adsorbed molecules as manifested by the SERS enhancement phenomenon. The exemplary SERS characterization implementations showed that for the exemplary nanotorch structures, the Raman enhancement effect of a single nanotorch does not depend on the coupling between multiple nanoparticles but rather on the resonant coupling of the sharp tips, inner cavity edges, and outer edges, which makes it an individual single SERS substrate. In the exemplary implementations, Raman measurements were then taken using a Renishaw in Via Raman microscope system with a 785-nm excitation source. Also, for example, measurements were also taken with a 532-nm source, but no signal was detected, as expected, since there is no plasmonic resonance at that wavelength. In the exemplary implementations, the substrates were immersed in the benezenethiol analyte and then rinsed and dried. At first, for example, a coarse Raman image mapping was performed on the sample using the built-in Raman imaging feature to ensure that it was the nanotorch structure being imaged. Next, for example, a 50× objective of the Raman imaging system was positioned over the hot spot seen on the image mapping and several static measurements were taken on and around the hot spot by moving the position of the substrate incrementally to maximize the Raman signal to ensure that the laser beam is focused on the nanotorch. The SERS enhancement factor is given by $$EF = \frac{I_{SERS}}{I_{neat}} \frac{N_{neat}}{N_{SERS}}$$

where $I_{SERS}$ and $N_{neat}$ refer to the peak intensities from the surface-adsorbed and the neat (bulk) benzenethiol analyte, respectively, $N_{SERS}$ and $N_{neat}$ refer to the number of molecules on the SERS surface and the neat benzenethiol interrogated, respectively, and n is the refractive index of benzenethiol. $N_{neat}$ can be defined as $$N_{neat} = \frac{\rho \cdot N_A \cdot n \cdot A \cdot h}{M_W}$$

where $\rho$ is the benzenethiol density, $N_A$ is Avogadro's number, $M_w$ is the molecular weight of the compound, A is the waist of the interrogating beam and h is the confocal depth parameter. The product of A×h represents the height of a cylindrical volume in which the signal generated by each neat benzenethiol molecule can be considered equal to the signal of a molecule found in the focal plane of the objective lens. $N_{SERS}$ can be defined as $$N_{SERA} = A \cdot F_{SERS} \cdot \mu_{SERS}$$

where $F_{SERS}$ is a ratio factor of the exposed SERS structure's surface area to the focused laser excitation. In the exemplary case, it is assumed that the exposed area is the hemisphere of a sphere with the equivalent radius of the nanotorch (e.g., ~205 nm), where $F_{SERS}$ is given by $$F_{SERS} = \frac{2\pi \cdot r_{sphere}^2}{\pi \cdot r_{beam}^2}.$$

Figure 13A:
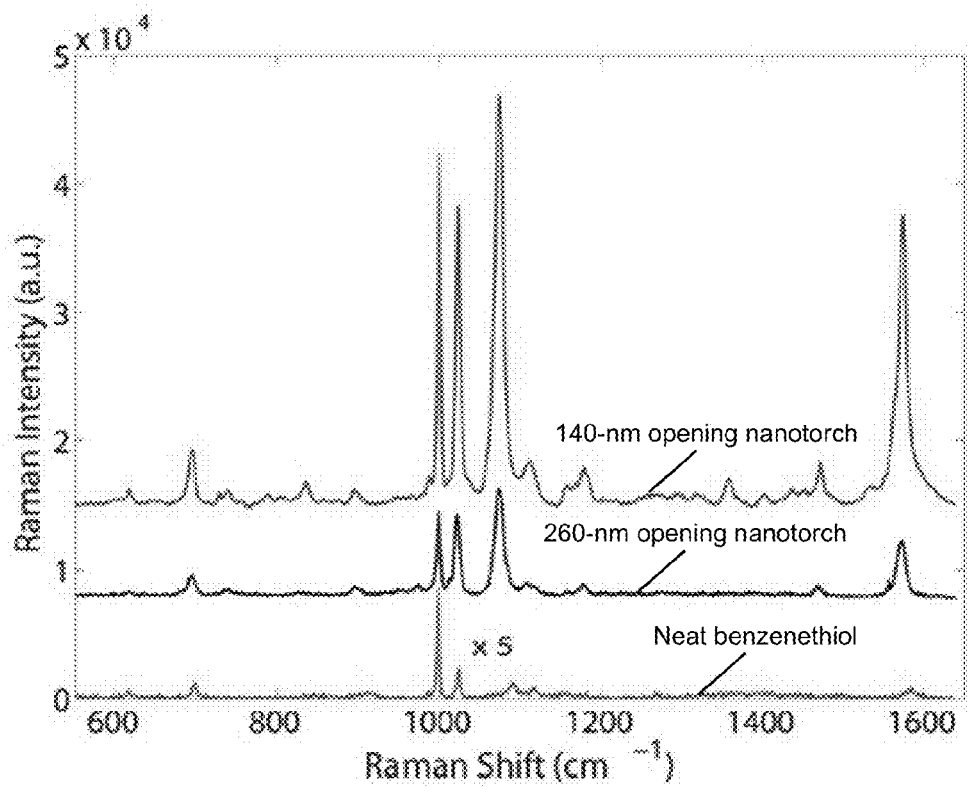
FIGS. 13A and 13B show exemplary Raman spectra plots using exemplary nanotorch structure-based SERS devices of the disclosed technology.

For example, if only a monolayer of benzenethiol exists on a flat gold surface, the surface coverage is equivalent to 0.6 nmol/cm$^2$. The Raman intensities of the 1573 cm$^{-1}$ band (C—C stretching mode) were considered, for example, to calculate the approximate enhancement factor because of its appearance in both the neat and SERS spectra. It is noted that for the neat spectrum, there is a slight shift for the neat Raman measurement to 1584 cm$^{-1}$. The Raman spectra are shown in FIG. 13A for the neat benzenethiol, which had been magnified 5 times to better show the modes, for the nanotorch with a 260-nm opening, and the nanotorch with a 140-nm opening for the bottom, middle, and top spectrum respectively. The modes of the spectra correspond to those of benzenethiol adsorbed onto gold, and the monolayer coverage of benzenethiol is confirmed by the absence of the C—S bond in the SERS spectra at around 2561 cm$^{-1}$ (not shown). No Raman signal was seen for measurement done on bare silicon sample sputtered with gold under the same sputtering condition. An exemplary estimate of the enhancement factor to be at least ~8.2×10$^6$ for the exemplary 140-nm opening nanotorch and 1.5×10$^6$ for the exemplary 260-nm opening nanotorch.

Figure 13B:
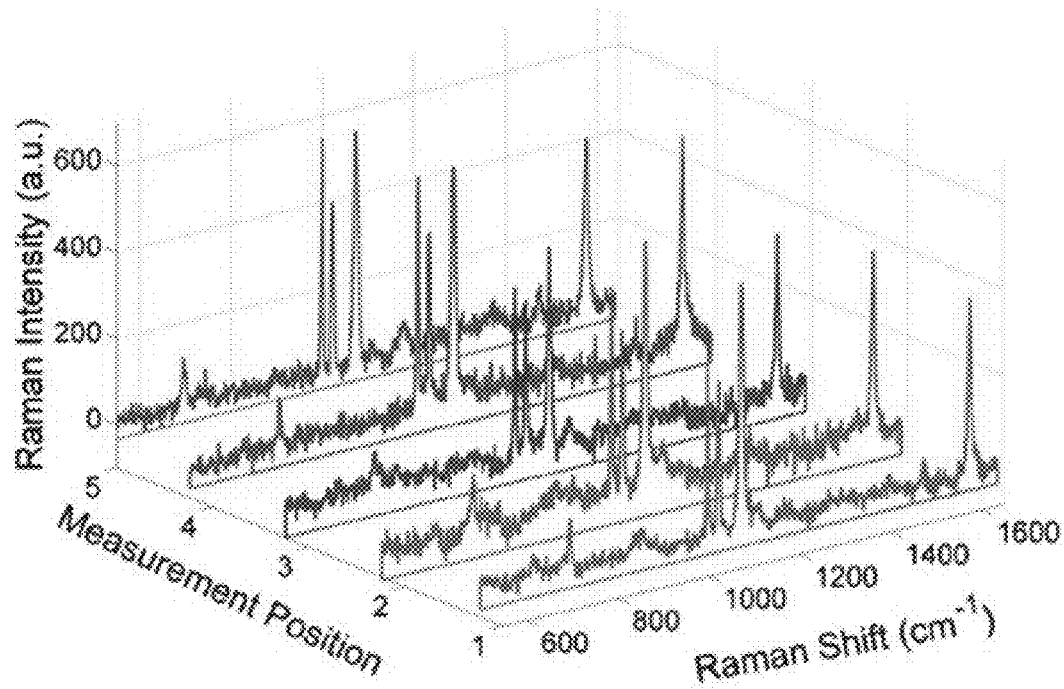

FIG. 13B shows an exemplary uniformity plot of five nanotorches at different locations within the same substrate device. As shown in FIG. 13B, a waterfall plot of the five Raman measurements showed that the standard deviations of the Raman intensity at each mode corresponding to 1000 cm$^{-1}$, 1023 cm$^{-1}$, 1074 cm$^{-1}$, and 1573 cm$^{-1}$ are all less than 20%, as shown in Table 1. The uniformity of the Raman intensity can be attributed to the upright orientation of the nanotorches and therefore, the consistent orientation of the incident field relative to the nanotorches.

Table 1 shows the standard deviation of Raman intensity for benzenethiol adsorb onto gold nanotorch.

TABLE 1

The standard deviation of the Raman intensity for benzenethiol adsorbed onto the gold nanotorch

| Peak [cm$^{-1}$] | Mode | Std. dev. |
| --- | --- | --- |
| 1000 | ν(C—C—C) | 20.0% |
| 1023 | ν(C—H) | 12.3% |
| 1074 | ν(C—C—C) and ν(C—S) | 12.6% |
| 1573 | ν(C—C—C) | 16.5% |

Figure 14A:
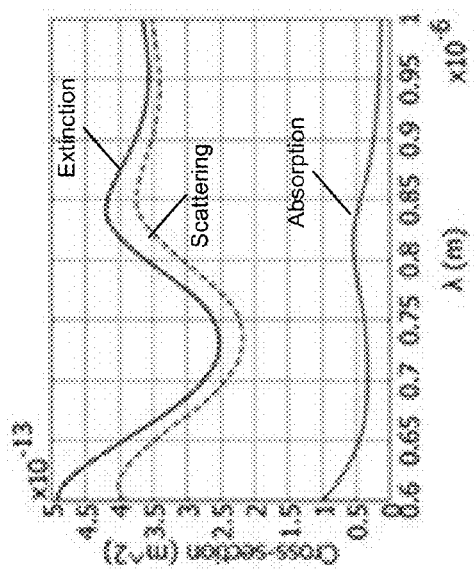
FIGS. 14A and 14B show data plots of the cross-section calculation of exemplary opening upright nanocrescent structures.
Figure 14B:
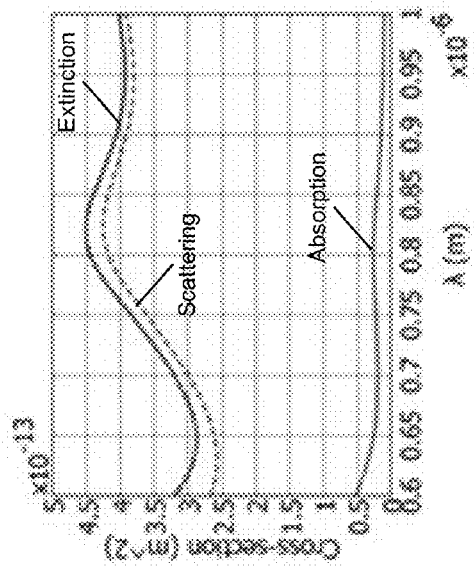

FIGS. 14A and 14B show data plots depicting the cross-section calculation of the exemplary 140-nm opening upright nanocrescent (FIG. 14A) and the exemplary 260-nm opening upright nanocrescent (FIG. 14B).

Figure 15A:
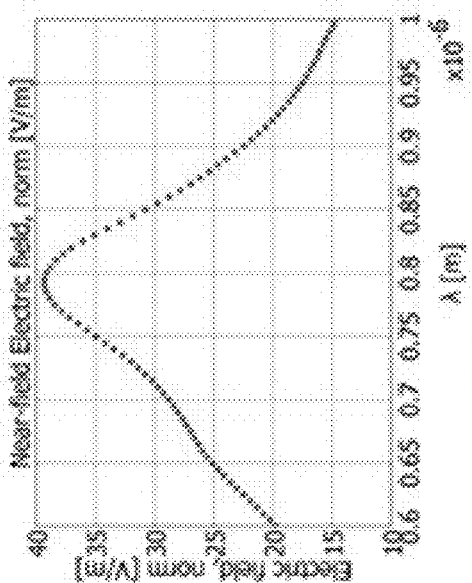
FIGS. 15A and 15B show data plots of the near-field electrical field versus wavelength at a single point on the rim of exemplary nanocrescent structures.
Figure 15B:
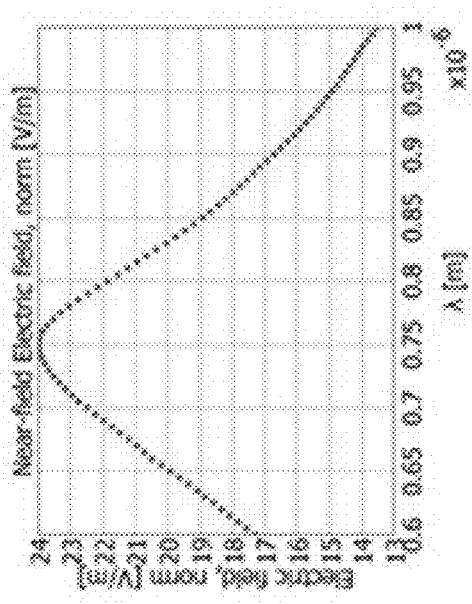

FIGS. 15A and 15B show data plots of the near-field electrical field versus wavelength at a single point on the rim of exemplary nanocrescent structures for the 140-nm opening (FIG. 15A) and 260-nm opening (FIG. 15B). The peak is shown to be around 785 nm, e.g. which means that the excitation of the laser used in the exemplary implementations was well-aligned to the plasmon resonance of the SERS structure.

As described above, the exemplary 3D FEM simulations of the disclosed nanotorch structured demonstrated that smaller cavity rim opening will produce higher local field enhancement and thus higher SERS enhancement factor.

Exemplary fabrication techniques were described to produce the disclosed upright nanotorch structures with controllable cavity opening and deterministic orientation, which can yield uniform Raman intensity of better than 80% for single nanoresonator. The disclosed SERS substrate devices including the exemplary nanotorch structures can be implemented such that each nanotorch serves as a single SERS substrate. In some implementations, the nanotorch structures can be configured with a 140-nm diameter rim opening, which yielded an enhancement factor of approximately 6 times higher than a larger rim opening (e.g., 260-nm diameter) as described in exemplary implementations. The higher enhancement factor of the disclosed 3D nanotorch structures can be used in a variety of application including in vivo diagnosis and single molecule detection.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described and other implementations, enhancements and variations can be made based on what is described and illustrated in this patent document.

What is claimed is:

1. A sensing device, comprising:
   a nanochip component structured to include a metal layer having an array of metal nanoholes that are separated from one another, a non-metal material layer formed on the metal layer and having an array of non-metal nanoholes that respectively align with the metal nanoholes to form an array of nanochannels that pass through the non-metal material layer and the metal layer to form openings at two sides of the nanochip component;
   a first substrate formed of an electrically insulative material on one side of the nanochip component and structured to include a first channel to carry a fluid containing particles;
   a second substrate formed of an electrically insulative material on the opposite side of the nanochip component to the first substrate and structured to include a second channel to carry the fluid;
   a plurality of electrodes configured in the first substrate and the second substrate, wherein at least some of the electrodes are located proximate to the ends of the first and second channels; and
   an electrical module that is electrically coupled to the electrodes and configured to apply an electric signal to at least one electrode in the first substrate and to at least one electrode in the second substrate to generate an electric field to effectuate an electrokinetic force within the channels to steer the particles toward the openings of the nanochannels to trap the particles,
   wherein the sensing device is operable to immobilize the particles at the openings of the nanochannels, and the nanochannels operate as resonant structures to amplify localized fields produced in an optical interrogation of the immobilized particles.

2. The device as in claim 1, wherein the particles include at least one of a nanoparticle, a microparticle, a molecule, a virus, or a cell.

3. The device as in claim 2, wherein the sensing device is operable to immobilize a single particle at the nanochannel.

4. The device as in claim 3, wherein the single immobilized particle or multiple immobilized particles are assembled at a respective nanochannel based on the effective index of refraction of the nanochannel, the effective index of refraction of the particle or particles, and depth within the respective nanochannel to which the single immobilized particle or multiple immobilized particles are trapped.

5. The device as in claim 1, wherein the metal nanoholes in the metal layer are structured to permit a single molecule of a size smaller than that of the opening to pass through the respective nanochannel.

6. The device as in claim 1, wherein the array of nanochannels is a periodic array such that the nanochip component is structured to support both propagating surface plasmon polariton (SPP) waves and localized surface plasmon resonant (LSPR) modes.

7. The device as in claim 1, wherein the array of nanochannels is an aperiodic or quasi-periodic array such that the nanochip component is structured to support LSPR modes.

8. The device as in claim 1, further comprising:
   a fluidic module that is fluidically coupled to the first and second channels to supply the fluid to the channels.

9. The device as in claim 8, wherein the fluidic module is configured to control the fluid to flow between the first and second substrates via the nanochannels of the nanochip component.

10. The device as in claim 9, wherein the controlled fluidic flow provides neutral fluidic pressure between the first and second channels.

11. The device as in claim 1, wherein the metal layer includes gold, the non-metal material includes a polymer material, and the first and second substrates include polydimethylsiloxane (PDMS).

12. The device as in claim 1, wherein the non-metal material includes a dielectric material.

13. The device as in claim 1, further comprising:
   an optical module that is coupled to supply light to the nanochip component to effectuate an optical trapping force to trap a molecule or particle at one end of a nanochannel.

14. The device as in claim 1, further comprising:
   an optical interrogation module that directs a coherent light beam on the nanochip component and detects inelastic scattering of the light beam by at least some of the trapped particles at the openings of the nanochannels to determine their Raman spectra,
   wherein the resonant structures amplify detected signals corresponding to the inelastic scattering.

15. A method for detecting a single molecule using the sensing device as in claim 14, the method comprising:

directing laser excitation light to the nanochip component of the sensing device to induce a localized surface plasmon resonance; and detecting an optical response signal caused by the localized surface plasmon resonance to extract information on the particles in the fluid in contact with the nanochannels.

16. A method to capture and characterize particles in a fluid, comprising:

transferring a fluid containing particles in a first channel of a nonconductive material formed over a composite membrane including an array of nanochannels that pass through two opposing sides of the composite membrane to a second channel of a nonconductive material formed on the opposing side of the composite membrane, wherein the first and second channels include a plurality of electrodes positioned proximate to the ends of the first and second channels;

selecting a frequency and magnitude of an electrical signal to be applied at the electrodes;

applying the electrical signal to generate an electric field to effectuate an electrokinetic force within the first and second channels to steer the particles toward the nanochannels to capture one or more particles at an opening or within a respective nanochannel;

directing a coherent light beam on the nanochannels of the composite membrane;

detecting, using an optical device, inelastic scattering of the light beam by at least some of the particles captured at the nanochannels, wherein the nanochannels operate as resonant structures to amplify localized fields produced by the inelastic scattering of the light beam of the captured particles; and determining a Raman spectra from the detected light.

17. The method as in claim 16, wherein the composite membrane is structured to include a metal layer having an array of metal nanoholes and a non-metal material layer attached to the metal layer and having an array of non-metal nanoholes that respectively align with the metal nanoholes to form the array of nanochannels.

18. The method as in claim 16, further comprising:

prior to the directing the coherent light beam, supplying light to the composite membrane to effectuate an optical trapping force to supplement or replace the electrokinetic force to trap one or more particles at an opening or within a respective nanochannel.

19. The method as in claim 16, further comprising:

prior to the applying the electric signal and using a fluidic module that is fluidically coupled to the first and second channels, controlling the fluid to flow through the nanochannels of the nanocomposite membrane to produce a neutral fluidic pressure between the first and second channels.

20. The method as in claim 16, wherein the array of nanochannels is a periodic array such that the composite membrane is structured to support both propagating surface plasmon polariton (SPP) waves and localized surface plasmon resonant (LSPR) modes.

21. The method as in claim 16, wherein the array of nanochannels is an aperiodic or quasi-periodic array such that the composite membrane is structured to support LSPR modes.

* * * * *